US011235069B2

(12) United States Patent
Mansour et al.

(10) Patent No.: US 11,235,069 B2
(45) Date of Patent: *Feb. 1, 2022

(54) USE OF LIPOSOMES IN A CARRIER COMPRISING A CONTINUOUS HYDROPHOBIC PHASE FOR DELIVERY OF POLYNUCLEOTIDES IN VIVO

(71) Applicant: IMMUNOVACCINE TECHNOLOGIES INC., Dartmouth (CA)

(72) Inventors: Marc Mansour, Halifax (CA); Mohan Karkada, Rockville, MD (US); Genevieve Mary Weir, Halifax (CA)

(73) Assignee: IMMUNOVACCINE TECHNOLOGIES INC., Dartmouth (CA)

( * ) Notice: Subject to any disclaimer, the term of this patent is extended or adjusted under 35 U.S.C. 154(b) by 5 days.

This patent is subject to a terminal disclaimer.

(21) Appl. No.: 16/254,716

(22) Filed: Jan. 23, 2019

(65) Prior Publication Data
US 2019/0224338 A1 Jul. 25, 2019

Related U.S. Application Data

(63) Continuation of application No. 15/290,567, filed on Oct. 11, 2016, now Pat. No. 10,232,052, which is a continuation of application No. 12/679,875, filed as application No. PCT/CA2008/001678 on Sep. 24, 2008, now Pat. No. 9,498,493.

(60) Provisional application No. 61/061,303, filed on Jun. 13, 2008, provisional application No. 60/975,602, filed on Sep. 27, 2007.

(51) Int. Cl.
A61K 48/00 (2006.01)
A61K 9/127 (2006.01)
C12N 15/88 (2006.01)
A61K 31/7088 (2006.01)
A61K 9/107 (2006.01)
A61K 38/20 (2006.01)
A61K 39/39 (2006.01)
C12N 15/113 (2010.01)
A61K 39/00 (2006.01)

(52) U.S. Cl.
CPC .......... A61K 48/0008 (2013.01); A61K 9/107 (2013.01); A61K 9/127 (2013.01); A61K 31/7088 (2013.01); A61K 38/208 (2013.01); A61K 39/39 (2013.01); C12N 15/1136 (2013.01); C12N 15/88 (2013.01); A61K 2039/55566 (2013.01); C12N 2310/14 (2013.01); C12N 2320/32 (2013.01)

(58) Field of Classification Search
CPC ...... A61K 31/7088; A61K 2039/55566; A61K 38/208; A61K 39/39; A61K 48/0008; A61K 9/107; A61K 9/127; C12N 15/1136; C12N 15/88; C12N 2310/14; C12N 2320/32
USPC ........... 424/450; 514/44 R, 44 A; 435/320.1, 435/325, 375, 455, 458
See application file for complete search history.

(56) References Cited

U.S. PATENT DOCUMENTS

| | | |
|---|---|---|
| 3,906,092 A | 9/1975 | Hilleman |
| 4,610,868 A | 9/1986 | Fountain et al. |
| 4,803,070 A | 2/1989 | Cantrell et al. |
| 4,806,350 A | 2/1989 | Gerber |
| 4,806,352 A | 2/1989 | Cantrell |
| 4,920,016 A | 4/1990 | Allen et al. |
| 5,013,556 A | 5/1991 | Woodle et al. |
| 5,015,476 A | 5/1991 | Cochrum et al. |
| 5,084,269 A | 1/1992 | Kullenberg |
| 5,340,588 A | 8/1994 | Domb |
| 5,422,109 A | 6/1995 | Brancq et al. |
| 5,545,412 A | 8/1996 | Eppstein et al. |
| 5,637,300 A | 6/1997 | Dunbar et al. |
| 5,662,931 A | 9/1997 | Munechika et al. |
| 5,688,772 A | 11/1997 | Estrada et al. |
| 5,705,151 A | 1/1998 | Dow et al. |
| 5,709,879 A | 1/1998 | Barchfeld et al. |
| 5,736,141 A | 4/1998 | Brown et al. |
| 5,820,879 A | 10/1998 | Fernandez et al. |
| 5,831,016 A | 11/1998 | Wang et al. |
| 5,844,075 A | 12/1998 | Kawakami et al. |
| 5,855,894 A | 1/1999 | Brown et al. |
| 5,863,549 A | 1/1999 | Tarantino |
| 5,897,873 A | 4/1999 | Popescu |
| 5,910,306 A | 6/1999 | Alving et al. |
| 5,919,480 A | 7/1999 | Kedar et al. |
| 5,980,898 A | 11/1999 | Glenn et al. |

(Continued)

FOREIGN PATENT DOCUMENTS

| | | |
|---|---|---|
| CA | 2078990 | 10/1991 |
| CA | 2082155 | 11/1991 |

(Continued)

OTHER PUBLICATIONS

Office Action regarding U.S. Appl. No. 14/674,063, dated Nov. 9, 2016 (29 pages).
Hearing Notice regarding related Indian application No. 411/MUMNP/2010, dated Sep. 30, 2016 (3 pgs.).
Examination Search Report from Canadian Patent Database 2,700,808 dated Apr. 22, 2016 Use of Liposomes in a Carrier Comprising a Continuous Hydrophobic Phase for Delivery of Polynucleotides in Vivo.

(Continued)

Primary Examiner — Janet L Epps-Smith
(74) Attorney, Agent, or Firm — Troutman Pepper Hamilton Sanders LLP

(57) ABSTRACT

The invention provides compositions comprising a carrier comprising a continuous phase of a hydrophobic substance, liposomes, and a polynucleotide, and methods for using such compositions for delivering a polynucleotide to a subject.

27 Claims, 3 Drawing Sheets

(56) References Cited

U.S. PATENT DOCUMENTS

| | | |
|---|---|---|
| 5,990,287 A | 11/1999 | Hosokawa et al. |
| 6,037,135 A | 3/2000 | Kubo et al. |
| 6,080,725 A | 6/2000 | Marciani |
| 6,090,406 A | 7/2000 | Popescu et al. |
| 6,093,406 A | 7/2000 | Alving et al. |
| 6,096,313 A | 8/2000 | Jager et al. |
| 6,110,492 A | 8/2000 | Alving et al. |
| 6,124,270 A | 9/2000 | Haensler |
| 6,168,804 B1 | 1/2001 | Samuel et al. |
| 6,183,746 B1 | 2/2001 | Urban et al. |
| 6,214,367 B1 | 4/2001 | Harvey |
| 6,218,371 B1 | 4/2001 | Krieg et al. |
| 6,228,648 B1 | 5/2001 | Condon et al. |
| RE37,224 E | 6/2001 | Brown et al. |
| 6,248,353 B1 | 6/2001 | Singh |
| 6,267,985 B1 | 7/2001 | Chen et al. |
| 6,284,267 B1 | 9/2001 | Aneja |
| 6,291,430 B1 | 9/2001 | Chaux et al. |
| 6,306,405 B1 | 10/2001 | O'Hagan et al. |
| 6,309,569 B1 | 10/2001 | Farrar et al. |
| 6,355,247 B1 | 3/2002 | Selby ................ C07K 14/005 424/188.1 |
| 6,355,256 B1 | 3/2002 | Noguchi et al. |
| 6,372,227 B1 | 4/2002 | Garcon et al. |
| 6,406,719 B1 | 6/2002 | Farrar et al. |
| 6,451,325 B1 | 9/2002 | Van Nest et al. |
| 6,464,980 B1 | 10/2002 | Fikes et al. |
| 6,468,558 B2 | 10/2002 | Wong |
| 6,472,159 B1 | 10/2002 | Darbouret et al. |
| 6,472,375 B1 | 10/2002 | Hoon et al. |
| 6,497,896 B2 | 12/2002 | Sands et al. |
| 6,511,676 B1 | 1/2003 | Boulikas |
| 6,517,816 B1 | 2/2003 | Gonzalez et al. |
| 6,528,058 B1 | 3/2003 | Edgar et al. |
| 6,534,064 B1 | 3/2003 | O'Hagan et al. |
| 6,537,966 B1 | 3/2003 | Duan et al. |
| 6,544,518 B1 | 4/2003 | Friede et al. |
| 6,565,777 B2 | 5/2003 | Farrar et al. |
| 6,572,861 B1 | 6/2003 | Roberts et al. |
| 6,588,671 B2 | 7/2003 | Liu et al. |
| 6,602,510 B1 | 8/2003 | Fikes et al. |
| 6,630,161 B1 | 10/2003 | Leesman |
| 6,632,447 B1 | 10/2003 | Steiner et al. |
| 6,649,172 B2 | 11/2003 | Johnson |
| 6,670,195 B1 | 12/2003 | Ghiso et al. |
| 6,676,958 B2 | 1/2004 | Gerber |
| 6,780,421 B1 | 8/2004 | Haensler et al. |
| 6,790,457 B1 | 9/2004 | Brown et al. |
| 6,793,923 B2 | 9/2004 | Brown et al. |
| 6,838,089 B1 | 1/2005 | Carlsson et al. |
| 6,881,405 B2 | 4/2005 | Leveugle et al. |
| 6,956,021 B1 | 10/2005 | Edwards et al. |
| 6,977,074 B2 | 12/2005 | Kündig et al. |
| 6,982,314 B2 | 1/2006 | Rosey |
| 7,019,112 B1 | 3/2006 | Slingluff et al. |
| 7,026,443 B1 | 4/2006 | Sette et al. |
| 7,037,509 B2 | 5/2006 | Koelle et al. |
| 7,056,515 B2 | 6/2006 | Brown et al. |
| 7,067,120 B2 | 6/2006 | Dianwen et al. |
| 7,087,236 B1 | 8/2006 | Brayden |
| 7,122,191 B2 | 10/2006 | Dominowski et al. |
| 7,148,191 B2 | 12/2006 | Egyed et al. |
| 7,179,645 B2 | 2/2007 | Humphreys et al. |
| 7,306,787 B2 | 12/2007 | Tarara et al. |
| 7,604,802 B2 | 10/2009 | O'Hagan |
| 7,611,721 B1 | 11/2009 | Hagen |
| 7,687,455 B2 | 3/2010 | Bonnet et al. |
| 7,824,686 B2 | 11/2010 | Brown et al. |
| 7,943,147 B2 | 5/2011 | Carter et al. |
| 9,498,493 B2 * | 11/2016 | Mansour ............ A61K 48/0008 |
| 10,232,052 B2 * | 3/2019 | Mansour ................ A61K 9/107 |
| 2002/0110568 A1 | 8/2002 | Brown et al. |
| 2003/0003105 A1 | 1/2003 | Gerber |
| 2003/0044454 A1 | 3/2003 | Fukui et al. |
| 2003/0161834 A1 | 8/2003 | Friede et al. |
| 2003/0185879 A1 | 10/2003 | Boulikas |
| 2003/0202979 A1 | 10/2003 | Gerber |
| 2003/0211115 A1 | 11/2003 | Gerber |
| 2003/0211140 A1 | 11/2003 | Mantripragada et al. |
| 2003/0220284 A1 | 11/2003 | Yotnda et al. |
| 2004/0170640 A1 | 9/2004 | Gerber |
| 2004/0202669 A1 | 10/2004 | O'Hagan |
| 2004/0213837 A1 | 10/2004 | Mantripragada et al. |
| 2004/0223977 A1 | 11/2004 | Diamond |
| 2004/0253731 A1 | 12/2004 | Holliger ................ A61K 9/107 435/458 |
| 2004/0258701 A1 | 12/2004 | Dominowski et al. |
| 2005/0002952 A1 | 1/2005 | Haensler et al. |
| 2005/0002999 A1 | 1/2005 | Mehta et al. |
| 2005/0013812 A1 | 1/2005 | Dow et al. |
| 2005/0019339 A1 | 1/2005 | Brown et al. |
| 2005/0037061 A1 | 2/2005 | Hosokawa et al. |
| 2005/0049197 A1 | 3/2005 | Sette et al. |
| 2005/0079208 A1 | 4/2005 | Albani |
| 2005/0084524 A1 | 4/2005 | Martin et al. |
| 2005/0118154 A1 | 6/2005 | Hung et al. |
| 2005/0158375 A1 | 7/2005 | Kimura et al. |
| 2005/0175683 A1 | 8/2005 | Zhang et al. |
| 2005/0202078 A1 | 9/2005 | Schiffelers et al. |
| 2005/0214322 A1 | 9/2005 | Garcon et al. |
| 2005/0220781 A1 | 10/2005 | Yan et al. |
| 2005/0220814 A1 | 10/2005 | Dominowski et al. |
| 2005/0249795 A1 | 11/2005 | Zhang et al. |
| 2005/0260643 A1 | 11/2005 | Hung et al. |
| 2005/0266066 A1 | 12/2005 | Uchida et al. |
| 2006/0008909 A1 | 1/2006 | Cullis et al. |
| 2006/0034908 A1 | 2/2006 | Bhamidipati et al. |
| 2006/0120997 A1 | 6/2006 | Lipton |
| 2006/0153844 A1 | 7/2006 | Kundig et al. |
| 2006/0182792 A1 | 8/2006 | Richardsen et al. |
| 2006/0183670 A1 | 8/2006 | Orban |
| 2006/0275777 A1 | 12/2006 | Waelti |
| 2006/0286038 A1 | 12/2006 | Rairkar et al. |
| 2007/0014805 A1 | 1/2007 | Dalencon et al. |
| 2007/0059318 A1 | 3/2007 | Balu-Iyer et al. |
| 2007/0082855 A1 | 4/2007 | Veldman et al. |
| 2007/0141078 A1 | 6/2007 | D'Hondt et al. |
| 2007/0212329 A1 | 9/2007 | Bruck et al. |
| 2007/0274980 A1 | 11/2007 | Balu-Iyer et al. |
| 2007/0298093 A1 | 12/2007 | Konur et al. |
| 2008/0014217 A1 | 1/2008 | Hanon et al. |
| 2008/0050395 A1 | 2/2008 | Gerber |
| 2009/0017057 A1 | 1/2009 | Chen et al. |
| 2009/0035266 A1 | 2/2009 | Schlom et al. |
| 2009/0074853 A1 | 3/2009 | Brown et al. |
| 2009/0081244 A1 | 3/2009 | Glenn et al. |
| 2009/0092666 A1 | 4/2009 | Brown et al. |
| 2009/0124549 A1 | 5/2009 | Lewinsohn et al. |
| 2009/0169636 A1 | 7/2009 | O'Hagan et al. |
| 2009/0247456 A1 | 10/2009 | Srivastava et al. |

FOREIGN PATENT DOCUMENTS

| | | |
|---|---|---|
| CA | 2086094 | 12/1991 |
| CA | 2115424 | 3/1993 |
| CA | 2183435 | 8/1995 |
| CA | 2205083 | 5/1996 |
| CA | 2137363 | 6/1999 |
| CA | 2436348 | 6/2002 |
| CA | 2523032 | 4/2007 |
| CA | 2542212 | 4/2007 |
| CA | 2533705 | 7/2007 |
| CN | 1473621 A | 2/2004 |
| EP | 0 640 347 | 3/1995 |
| EP | 1333858 | 2/2006 |
| GB | 2134869 | 8/1984 |
| JP | 09-25238 | 1/1997 |
| JP | 2002-532163 A | 10/2002 |
| JP | 2004-525115 | 8/2004 |
| JP | 2007-532629 | 11/2007 |
| WO | WO 92/00081 | 1/1992 |
| WO | WO 92/10513 | 6/1992 |
| WO | WO 93/25231 | 12/1993 |
| WO | WO 1995/31480 | 11/1995 |

(56) References Cited

FOREIGN PATENT DOCUMENTS

| WO | 96/014871 A1 | 5/1996 | |
|---|---|---|---|
| WO | 98/53799 A2 | 12/1998 | |
| WO | 99/27944 A1 | 8/1999 | |
| WO | WO 2000/37100 | 6/2000 | |
| WO | 200238175 A1 | 5/2002 | |
| WO | WO 2002/38175 | 5/2002 | |
| WO | WO-0238175 A1 | 5/2002 | ............ A61K 9/127 |
| WO | WO 0238175 A1 | 5/2002 | |
| WO | 02/070006 A2 | 9/2002 | |
| WO | WO 2003/066680 | 8/2003 | |
| WO | 2004/000873 A2 | 12/2003 | |
| WO | WO 2004/052917 | 6/2004 | |
| WO | WO 2004/058179 | 7/2004 | |
| WO | WO 2004/094454 | 11/2004 | |
| WO | 2005/025614 A2 | 3/2005 | |
| WO | WO 2005/019435 | 3/2005 | |
| WO | 2005/072777 A2 | 8/2005 | |
| WO | WO 2005/089164 | 9/2005 | |
| WO | 2006/050155 A2 | 5/2006 | |
| WO | 2006113679 A2 | 10/2006 | |
| WO | WO 2006/113679 | 10/2006 | |
| WO | WO2006/113679 A2 * | 10/2006 | |
| WO | 2007041832 A1 | 4/2007 | |
| WO | WO 2007/041832 | 4/2007 | |
| WO | WO2007/041832 A1 * | 4/2007 | |
| WO | WO 2007/071707 | 6/2007 | |
| WO | WO 2007/071710 | 6/2007 | |
| WO | WO 2007/071711 | 6/2007 | |
| WO | 2008/000261 A2 | 1/2008 | |
| WO | 2009/043165 A1 | 4/2009 | |

OTHER PUBLICATIONS

Sigma-Aldridch—Product Information Frueund's Adjuvant Complete and Incomplete Catalog Numbers F5881 and F5506.
Examination report regarding Canadian counterpart application No. 2,700,808, dated Feb. 9, 2015 (10 pgs.).
Wu H. et al., Int J Pharm, vol. 221, pp. 23-34, Jun. 19, 2001 (12 pgs.).
Chung et al., "Oil Components Modulate Physical Characteristics and Function of the Natural Oil Emulsions a Drug or Gene Delivery System," Jn'l Cont. Rel., 71: 339-350, 2001.
Choi et al., "Low Toxicity of Cationic Lipid-Based Emulsion for Gene Transfer," Biomaterials, 25:5893-5903, 2004.
Zheng et al., A Novel DNA Vaccine Based on Ubiquitin-Proteasome Pathway Targeting Self-Antigens Expressed in Melanoma/Melanocyte; Gene Therapy (2005) 12, 1049-1057.
U.S. Office Action for related U.S. Appl. No. 12/992,512 dated Oct. 18, 2012.
Supplementary European Search Report for related Application No. EP 08 80 0369 dated Apr. 20, 2012.
Karkuda et al., "A liposome-based platform, VacciMax, and its modified water-free platform DepoVax enhance efficacy in vivo nucleic acid delivery", Vaccine, Elsevier Ltd, GB, vol. 28, No. 38, Aug. 31, 2010, pp. 6176-6182.
Meyer Martin et al., "Recent developments in the application of plasmid DNA-based vectors and small interfering RNA therapeutics for cancer", Human Gene Therapy, vol. 17, No. 11, Nov. 2006, pp. 1062-1076.
Adam, J.K. et al., "Immune responses in cancer", Pharmacol. Ther., (2003) p. 113-132, vol. 99.
Agger, E.M. et al, "Protective immunity to tuberculosis with Ag85B-ESAT-6 in a synthetic cationic adjuvant sytem IC31", Vaccine, (2006) p. 5452-5460, vol. 24.
Alexander, J. et al., "Development of high potency universal DR-restricted helper epitopes by modification of high affinity DR-blocking peptides", Immunity (1994) p. 751-761, vol. 1.
Alexopoulou, L. et al., "Recognition of double-stranded RNA and activation of NF-kappaB by Toll-like receptor 3", Nature, (2001) p. 732-738, vol. 413.

Allegra, C.J. et al., "Cytotoxins and cancer immunotherapy: The dance of the macabre?", J. National Cancer Institute, (2005) p. 1396-1397, vol. 97.
Altschul, S.F. et al,, "Basic Local Alignment Search Tool", J. Mol. Biol., (1990) p. 403-410, vol. 215.
Alving, C.R., "Design and selection of vaccine adjuvants: animal models and human trials", Vaccine, (2002) p. S56-S64, vol. 20.
Antonia, S.J. et al., "Combination of p53 cancer vaccine with chemotherapy in patients with extensive state small cell lung cancer" Clinical Cancer Research, (2006) p. 878-887, vol. 12.
Awasthi, A. et al., "Poly ICLC enhances the antimalarial activity of chloroquine against multidrug-resistant Plasmodium yoelil nigeriensis in mice", J Interferon Cytokine Res., (1997) p. 419-423, vol. 17.
Bagavant et al., "Antifertility effects of porcine zona pellucida-3 immunization using permissible adjuvants in female bonnet monkeys (*Macaca radiata*): reversibility, effect on follicular development and hormonal profiles", J. Reprod. Fertil., (1994) p. 17-25, vol. 102.
Banga, A.K., Therapeutic Peptides and Proteins, Formulations, Processing and Delivery Systems, (1995), Technomic Publishing, Co., Lancaster, PA.
Bellone, M. et al., "Revelance of the tumor antigen in the validation of three vaccination strategies for melanoma", Journal of Immunology, (2000) p. 2651-2656, vol. 165, No. 5.
Bever, C.T. et al., "Preliminary trial of poly ICLC in chronic progressive multiple sclerosis", Neurology, (1986) p. 494-498, vol. 36.
Bobst, A.M. et al., "Interferon induction by poly(inosinic acid),poly(cytidylic acid) segmented by spin-labels", Biochemistry, (1981) p. 4798-4803, vol. 20.
Bosch, F.X. et al., "Prevalence of human papillomavirus in cervical cancer: a worldwide perspective", J. Natl. Cancer Inst., (1995) p. 796-802, vol. 87.
Bronte, V. et al., "Genetic Vaccination with "Self" Tyrosinase-related Protein 2 Causes Melanoma Eradication but not Vitiligo", Cancer Research, (Jan. 15, 2000) p. 253-258, vol. 60.
Brown, R.G. et al., "Evidence for a long-lasting single administration contraceptive vaccine in wild grey seals", J. Reprod. Immunol., (1997) p. 43-51, vol. 35.
Brown, R.G. et al., "Temporal trends in antibody production in captive grey, harp and hooded seals to a single administration immunocontraceptive vaccine", J. Reprod. Immunol., (1997) p. 53-64, vol. 35.
Cassarino, D.S. et al., "The effects of gp100 and tyrosinase peptide vaccinations on nevi in melanoma patients", J. Cutaneous Path., (2006) p. 335-342, vol. 33.
Celis E. et al., "Recognition of hepatitis B surface antigen by human T lymphocytes. Proliferative and cytotoxic responses to a major antigenic determinant defined by synthetic peptides", Journal of Immunology, (1988) p. 1808-1815, vol. 140.
Chakraborty, M. et al., "External beam radiation of tumors alters phenotype of tumor cells to render them susceptible to vaccine-mediated T-cell killing", Cancer Research, (2004) p. 4328-4337, vol. 64.
Chen, Y.F. et al., "Cytotoxic-T-lymphocyte human papillomavirus type 16 E5 peptide with CpG-oligodeoxynucleotide can eliminate tumor growth in C57BL/6 mice", J. Virol. (Feb. 2004) p. 1333-1343, ISSN 0022-538X, vol. 78, No. 3.
Chikh, G. et al., "Liposomal delivery of CTL epitopes to dendritic cells", Biosci. Rep. (Apr. 2002) p. 339-353, ISSN 0144-8463, vol. 22, No. 2.
Chirigos, M.A. et al., "Pharmacokinetic and therapeutic activity of polyinosinic-polycytidylic acid stabilized with poly-L-lysine in carboxymethylcellulose [poly(1,C)-LC]", J Biol Response Mod, (1985) p. 621-627, vol. 4.
Chong P. et al., "Identification of T- and B-cell epitopes of the S2 and S3 subunits of pertussis toxin by use of synthetic peptides", Infection and Immunity, (1992) p. 4640-4647, vol. 60.
Copland, M.J. et al., "Lipid based particulate formulations for the delivery of antigen", Immunol. Cell Biol., (2005) p. 97-105, vol. 83.

(56) References Cited

OTHER PUBLICATIONS

Correale, P. et al., "Fluorouracil-based chemotherapy enhances the antitumor activity of a thymidylate synthase-directed polyepitopic peptide vaccine", Journal of the National Cancer Institute, (2005) p. 1437-1445, vol. 97.
Cox, J.C. et al., "Adjuvants—a classification and review of their modes of action", Vaccine, (1997) p. 248-256, vol. 15, No. 3.
Cui Z. et al., "Liposome-polycation-DNA (LPD) particle as a carrier and adjuvant for protein-based vaccines: Therapeutic effect against cervical cancer", Cancer Immunol. Immunother. (2005) p. 1180-1190, vol. 54.
Cui, Z. & Qui, F., "Synthetic double-stranded RNA poly(I:C) as a potent peptide vaccine adjuvant: therapeutic activity against human cervical cancer in a rodent model", Cancer Immunol Immunother, (2006) p. 1267-1269, vol. 55.
Da Silva, D.M. et al., "Heterologous boosting increases immunogenicity of chimeric papillomavirus virus-like particle vaccines", Vaccine, (2003) p. 3219-3227, vol. 21.
Daftarian, P. et al., "Eradication of established HPV 16-expressing tumors by a single administration of a vaccine composed of a liposome-encapsulated CTL-T helper fusion peptide in a water-in-oil emulsion", Vaccine (2006) p. 5235-5244, vol. 24, No. 24.
Daftarian, P. et al., "Two distinct pathways of immuno-modulation improve potency of p53 immunization in rejecting established tumors", Cancer Res., (2004) p. 5407-5414, vol. 64.
Daftarian, P. et al., "Rejection of large HPV-16 expressing tumours in aged mice by a single immunization of VacciMax® encapsulated CTL/T helper peptides", J. Trans. Med., (Jun. 2007), p. 1-9, vol. 5, No. 26.
Davis, H.L. et al., "CpG DNA is a Potent Enhancer of Specific Immunity in Mice Immunized with Recombinant Hepatitis B Surface Antigen", J. Immunol., (1998) p. 870-876, vol. 160.
De Clercq, E. et al, "Antiviral activity of polynucleotides: copolymers of inosinic acid and N2-dimethylguanylic of 2-methylthioinosinic acid", Nucleic Acids Res, (1975) p. 121-129, vol. 2.
De Clercq, E. et al., "Interferon induction by a 2'-modified double-helical RNA, poly(2'-azido-2'-deoxyinosinic acid), polycytidylic acid", Eur J Biochem. (1978) p. 341-349, vol. 88.
Demotz S. et al., "Delineation of serveral DR-restricted tetanus toxin T cell epitopes", Journal of Immunology, (1989) p. 394-402, vol. 142.
Diethelm-Okita, B.M. et al., "Universal epitopes for human CD4+ cells on tetanus and diphtheria toxins", Journal of Infectious Diseases, (2000) p. 1001-1009, vol. 181.
Dong, L.W. et al., "Single regulatory protein alpha negatively regulates both TLR3 and cytoplasmic pathways in type 1 interferon induction", Mol Immunol, (2008) p. 3025-3035, vol. 45.
Dudley, M.E. et al., "Adoptive transfer of cloned melanoma-reactive T lymphocytes for the treatment of patients with metastatic melanoma", Journal of Immunotherapy, (2001) p. 363-373, vol. 24, No. 4.
Durie, B.G. et al., "Poly(I,C)-LC as an interferon inducer in refractory multiple myeloma", J Biol Response Mod, (1985) p. 518-524, vol. 4.
Edelman et al., "Adjuvants", Intern. Rev. Immunol., (1990) p. 51-66, vol. 7, No. 1.
Fagerstone, K. A. et al., "Wildlife Fertility Control", The Wildlife Society Technical Review 02-2, (2002) p. 1-29, University of Nebraska—Lincoln.
Fausch, S.C. et al., "Human Papillomavirus Can Escape Immune Recognition through Langerhans Cell Phosphoinositide 3-Kinase Activation", J. Immunol., (2005) p. 7172-7178, vol. 174.
Feltkamp, M.C. et al., "Vaccination with cytotoxic T lymphocyte epitope-containing peptide protects against a tumor induced by human papillomavirus type 16-transformed cells", Eur. J. Immunol., (1993) p. 2242-2249, vol. 23.
Fernando, G.J. et al., "Vaccine-induced Th1-type responses are dominant over Th2-type responses in the short term whereas pre-existing Th2 responses are dominant in the longer term", Scandinavian Journal of Immunology, (1998) p. 459-465, vol. 47 No. 5.

Fraker, M.A. et al., "Long-Lasting, Single-Dose Immunocontraception of Feral Fallow Deer in British Columbia", J. Wildl. Manage., (2002) p. 1141-1147 vol. 66.
Frazer, I.H., "Prevention of cervical cancer through papillomavirus vaccination", Nat. Rev. Immunol., (2004) p. 46-54, vol. 4.
Frey, A. et al., "A statistically defined endpoint titer determination method for immunoassays", J Immunol Methods, (1998) p. 35-41, vol. 221.
Frezard, F., "Liposomes: from biophysics to the design of peptide vaccines", Brazilian Journal of Medical Biology and Research, (1999) p. 181-189, vol. 32.
Fujimura, T. et al., "Inhibitory effect of the polyinosinic-polycytidylic acid/cationic liposome on the progression of murine B16F10 melanoma", Eur J Immunol, (2006) p. 3371-3380, vol. 36.
Fukui, T. et al., "XLV Synthesis and properties of poly(2'-azido-2'-deoxyinosinic acid)", Nucleic Acids Res., (1977) p. 2629-2639, vol. 4.
Gerard, C.M. et al., "Therapeutic potential of protein and adjuvant vaccinations on tumour growth", Vaccine, (2001) p. 2583-2589, vol. 19.
Gillison, M.L., "Human papillomavirus-associated head and neck cancer is a distinct epidemiologic, clinical, and molecular entity", Semin. Oncol., (2004) p. 744-754, vol. 31.
Goedert, M. et al., "A Century of Alzheimer's Disease", Science, (2006) p. 777-81, vol. 314.
Gorman, S.P. et al., "Evaluation of a porcine zona pellucida vaccine for the immunocontraception of domestic kittens (*Fells catus*)", Theriogenology, (2002) p. 135-149, vol. 58.
Gowen, B.B. et al., "TLR3 is essential for the induction of protective immunity against Punta Toro Virus infection by the double-stranded RNA (dsRNA), poly(1:C12U), but not Poly(I:C): differential recognition of synthetic dsRNA molecules", J Immunol, (2007) p. 5200-5208, vol. 178.
Greene, J.J. et al., "Interferon induction and its dependence on the primary and secondary structure of poly(inosinic acid). poly(cytidylic acid)", Biochemistry, (1978) p. 4214-4220, vol. 17.
Gregoriadis, G., "Immunological adjuvants: A role for liposomes", Immunology Today, (1990) p. 89-97, vol. 11, No. 3.
Gulley, J.L. et al., "Combining a recombinant cancer vaccine with standard definitive radiotherapy in patients with localized prostate cancer", Clinical Cancer Research, (2005) p. 3353-3362 vol. 11.
Gupta et al., "Adjuvants—a balance between toxicity and adjuvanticity", Vaccine, (1993) p. 293-306, vol. 11, No. 13.
Gupta, R. et al., "Adjuvants for human vaccines—current status, problems and future prospects", Vaccine, (1995) p. 1263-1276, vol. 13, No. 14.
Guschlbauer, W. et al., "Poly-2'-deoxy-2'-fluoro-cytidylic acid: enzymatic synthesis, spectroscopic characterization and interaction with poly-inosinic acid", Nucleic Acids Res, (1977) p. 1933-43, vol. 4.
Guy, B. "The perfect mix: recent progress in adjuvant research", Nat Rev Microbiol., (2007) p. 505-517, vol. 5.
Harada, M. et al., "Vaccination of cytotoxic T lymphocyte-directed peptide elicited and spread humoral and Th1-type immune responses to prostate-specific antigen protein in a prostate cancer patient", J. Immunother. (Jul.-Aug. 2005) p. 368-375, ISSN 1524-9557, vol. 28, No. 4.
Harrenstien, L.A. et al., "Effects of Porcine Zona Pellucida Immunocontraceptive in Zoo Felids", J. Zoo Wildlife Medicine, (2004) p. 271-279, vol. 35.
Hendrix, C.W. et al., "Biologic effects after a single dose of poly(1):poly(C12U) in healthy volunteers", Antimicrob. Agents Chemother., (1993) p. 429-435, vol. 37.
Hilbert, A. et al., "Biodegradable microspheres containing influenza A vaccine: immune response in mice", Vaccine, (1999) p. 1065-1073, vol. 17, No. 9-10.
Houston, W.E. et al., "Modified polyriboinosinic-polyribocytidylic acid, an immunological adjuvant", Infect Immun. (1976) p. 318-319, vol. 14.
Husbrand, A.J., "Novel vaccination stratetis for the control of mucosal infection", Vaccine, (1993) p. 107-112 vol. 11, No. 2 (abstract only).

(56) References Cited

OTHER PUBLICATIONS

Ichinohe, T. et al., "Cross-protection against H5N1 influenza virus infection is afforded by intranasal inoculation with seasonal trivalent inactivated influenza vaccine", J Infect Dis., (2007) p. 1313-1320, vol. 196.
Itoh, T. et al., "Transcutaneous immunization with cytotoxic T-cell peptide epitopes provides effective antitumor immunity in mice", J. Immunother., (2005) p. 430-437, vol. 28.
Itzhaki, R.F. et al., "Simplex Virus Type 1 in Alzheimer's Disease: The Enemy Within", J Alzheimers Dis., 2008 p. 393-405, vol. 13.
Ivanova et al., "Contraceptive potential of porcine zona pellucida in cats", Theriogenology, (1995) p. 969-981, vol. 43.
Jentoft, N. et al., "Labeling of proteins by reductive methylation using sodium cynoborohydride", J. Biol. Chem., (1979) p. 4359-4365, vol. 254, No. 11.
Jerome, V. et al, "Cytotoxic T lymphocytes responding to low dose TRP2 antigen are induced against B16 melanoma by liposome-encapsulated TRP2 peptide and CpG DNA adjuvant", J. Immunother., (2006) p. 294-305, vol. 29, No. 3.
Jin, B. et al, "Induction of potent cellular immune response in mice by hepatitis C virus NS3 protein with double-stranded RNA", Immunology, (2007) p. 15-27, vol. 122.
Johnston, M.I. et al., "Structural features of double-stranded polyribonucleotides required for immunological specificity and interferon induction", Proc Natl Acad Sci USA, (1975) p. 4564-4568, vol. 72.
Kadowaki, N. et al., "Subsets of human dendritic cell precursors express different toll-like receptors and respond to different microbial antigens", J. Exp. Med., (2001) p. 863-869, vol. 194.
Kamath, A.T. et al., "Protective anti-mycobacterial T cell responses through exquisite in vivo activation of vaccine-targeted dendritic cells", Eur J Immunol., (2008) p. 1247-1256, vol. 38.
Kawaoka, Y. et al., "Molecular Characterization of a New Hemagglutinin, Subtype H14, of Influenza A Virus", Virology, (1990) p. 759-767, vol. 179.
Kende, M. et al., "Ranking of prophylatic efficacy of poly(ICLC) against Rift Valley fever virus infection in mice by incremental relative risk of death", Antimicrob Agents Chemother., (1987) p. 1194-1198, vol. 31.
Knutson, K.L., et al., "Immunization of cancer patients with a HER-2/neu, HLA-A2 peptide, p. 369-377, results in short-lived peptide-specific immunity", Clinical Cancer Research, (2002) p. 1014-1018, vol. 8, No. 5.
Koutsky, L.A. et al., "A controlled trial of a human papillomavirus type 16 vaccine", N. Engl. J. Med., (2002) p. 1645-1651, vol. 347.
Krown, S.E. et al., "Phase I trials of poly(I,C) complexes in advanced cancer", J Biol Response Mod, (1985) p. 640-649, vol. 4.
Lambros, M.P. et al., "Liposomes, a potential immunoadjuvant and carrier for a cryptococcal vaccine", J. Pharmaceutical Sciences, (Sep. 1998), p. 1144-1148, vol. 87, No. 9.
Levy, H.B. "Historical overview of the use of polynucleotides in cancer", J Biol Response Mod., (1985) p. 475-480, vol. 4.
Levy, H.B. et al., "Topical treatment of vaccinia virus infection with an interferon inducer in rabbits", J Infect Dis., (1978) p. 78-81, vol. 137.
Levy, J.K. et al., "Survey of zona pellucida antigens for immunocontraception of cats", Theriogenology, (2005) p. 1334-1341, vol. 63.
Liang, M.T. et al., "Particulate systems as adjuvants and carriers for peptide and protein antigens", Current Drug Delivery, (2006), p. 379-388, vol. 3.
Llopiz, D. et al., "Combined immunization with adjuvant molecules poly(I:C) and anti-CD40 plus a tumor antigen has potent prophylactic and therapeutic antitumor effects", Cancer Immunol Immunother, (2008) p. 19-29, vol. 57.
Mansour, M. et al., "Therapy of Established B16-F10 Melanoma Tumours by a Single Vaccination of CTL/T Helper Peptides in VacciMax®", J. Transl. Med., (Apr. 2007), p. 1-8, vol. 5, No. 20.

Mansour, M. et al., "Improved efficacy of a licensed acellular pertossis vaccine, reformulated in an adjuvant emulsion of liposomes in oil, in a murine model", Clin. and Vaccine Immunol., (Oct. 2007), p. 1381-1383, vol. 14, No. 10.
Matthews, L.J. et al., "Immunogenically fit subunit vaccine components via epitope discovery from natural peptide libraries", J. Immunol, (2002) p. 837-846, vol. 169.
Mayordomo, J.I. et al., "Bone marrow-derived dendritic cells pulsed with synthetic tumour peptides elicit protective and therapeutic antitumour immunity", Nat. Med., (1995) p. 1297-1302, vol. 1.
Millan, C.L.B. et al., "CpG DNA can induce strong Th1 humoral and cell-mediated immune response against hepatitis B surface antigen in young mice", PNAS, (1998) p. 15553-15558, vol. 95.
Mosmann, T.R., "Role of a New Cytokine, Interleukin-10, in the Cross-Regulation of T Helper Cells", Acad. Sci. (1991) p. 337-344, vol. 628.
Muderhwa, J.M. et al., "Oil-in-water liposomal emulsions: characterization and potential use in vaccine delivery", J. Pharm. Sci. (Dec. 1999) p. 1332-1339, ISSN 0022-3549, vol. 88, No. 12.
Muttilainen, S. et al., "The *Neisseria meningitidis* outer membrane protein P1 produced in *Bacillus subtilis* and reconstituted into phospholipid vesicles elicits antibodies to native P1 epitopes", Microbial Pathogenesis, (1995) p. 423-436, vol. 18.
Nakamura, O. et al., "Phase I-II trials of poly(ICLC) in malignant brain tumor patients", J Interferon Res, (1982) p. 1-4, vol. 2.
Nash et al., "Formulation of a potential antipregnancy vaccine based on the b-subunit of human chorionic gonadotropin (b-hCG). II. Use of compounds of the muramyl dipeptide (MDP) family as adjuvants", J. Reprod. Immunol., (1985) p. 151-162, vol. 7, No. 2.
Needleman, S.B. and Wunsch, C.D. "A General Method Applicable to the Search for Similarities in the Amino Acid Sequence of Two Proteins", J. Mol. Biol., (1970) p. 443-453, vol. 48.
Ohlschläger, P. et al., "Human Papillomavirus Type 16 L1 Capsomeres Induce L1-Specific Cytotoxic T Lymphocytes and Tumor Regression in C57BL/6 Mice", Journal of Virology (2003) p. 4635-4645, vol. 77.
Padalko, E. et al., "The interferon inducer ampligen [poly(1)-poly(C12U)] markedly protects mice against coxsackie B3 virus-induced myocarditis", Antimicrob Agents Chemother, (2004) p. 264-274, vol. 48.
Padilla-Paz, L.A., "Human papillomavirus vaccine: history, immunology, current status, and future prospects", Clin. Obstet. Gynecol., (2005) p. 226-240, vol. 48.
Parkin, D.M. et al., "Estimating the world cancer burden: Globocan 2000", Int. J. Cancer, (2001) p. 153-156, vol. 94.
Parrado et al., "The domain organization of streptokinase: Nuclear magnetic resonance, circular dichroism, and functional characterization of proteolytic fragments", Protein Sci., (1996) p. 693-704, vol. 5.
Pilon-Thomas, S. et al., "Immunostimulatory Effects of CpG-ODN Upon Dendritic Cell-Based Immunotherapy in a Murine Melanoma Model", Journal Immunotherapy, (2006) p. 381-387, vol. 29, No. 4.
Poast, J. et al., "Poly ECLC induction of the interferon system in mice: an initial study of four detection methods", J Interferon Cytokine Res, (2002) p. 1035-1040, vol. 22.
Puri, S.K. et al., "Poly ICLC inhibits Plasmodium cynomolgi B malaria infection in rhesus monkeys", J Interferon Cytokine Res., (1996) p. 49-52, vol. 16.
Pye, D. et al., "Selection of an adjuvant for vaccination with the malaria antigen, MSA-2", Vaccine, (1997) p. 1017-1023, vol. 15, No. 9.
Rao, M. et al., "Delivery of lipids and liposomal proteins to the cytoplasm and Golgi of antigen presenting cells", Adv. Drug Deliv. Rev., (2000) p. 171-188, vol. 41.
Rao, M. et al., "Intracellular processing of liposome-encapsulated antigens by macrophages depends upon the antigen", Infect. Immun., (1995) p. 2396-2402, vol. 63.
Reis E Sousa, C., "Toll-like receptors and dendritic cells: for whom the bug tolls", Semin. Immunol., (2004) p. 27-34, vol. 16.
Riedl, K. et al., "The novel adjuvant IC31® strongly improves influenza vaccine-specific cellular and humoral immune responses in young adult and aged mice", Vaccine, (2008) p. 3461-3468, vol. 26.

(56) References Cited

OTHER PUBLICATIONS

Roberge, J.Y. et al., "A Strategy for a Convergent Synthesis of N-Linked Glycopeptides on a Solid Support", Science, (1995) p. 202-204, vol. 269.

Salazar, A.M. et al., "Long-term treatment of malignant gliomas with intramuscularly administered poluyinosinic-polyeytidylic and stabilized with polylysine and carboxymethylcellulose: an open pilot study", Neurosurgery, (1996) p. 1096-103 and discussion 1103-1104, vol. 38.

Salem, M.L. et al., "The adjuvant effects of the toll-like receptor 3 ligand polyinosinic-cytidylic acid poly(I:C) on antigen-specific CD8+ T cell responses are partially dependent on NK cells with the induction of a beneficial cytokine milieu", Vaccine, (2006) p. 5119-5132, vol. 24.

Salem, M.L. et al., "Defining the antigen-specific T-cell response to vaccination and poly(I:C)/TLR3 signaling: evidence of enhanced primary and memory CD8 T-cell responses and antitumor immunity", J. Immunother, (2005) p. 220-228, vol. 28.

Sarma, P.S. et al.,"Virus-induced sarcoma of mice: inhibition by a synthetic polyribonucleotide complex", Proc Natl Acad Sci USA, (1969) p. 1046-1051, vol. 62.

Schellack, C. et al., "IC31, a novel adjuvant signaling via TLR9, induces potent cellular and humoral immune responses", Vaccine, (2006) p. 5461-5472, vol. 24.

Schijns, V.E., "Immunological concepts of vaccine adjuvant activity", Current Opinion in Immunology, (2000) p. 456-463, vol. 12.

Schreckenberger, C. et al., "Vaccination strategies for the treatment and prevention of cervical cancer", Curr. Opin. Oncol., (2004) p. 485-491, vol. 16.

Schueler-Furman, O. et al., "Knowledge-based structure prediction of MHC class I bound peptides: a study of 23 complexes", Folding & Design, (1998) p. 549-564, vol. 3.

Shedlock, D.J. et al., "Requirement for CD4 T cell help in generating functional CD8 T cell memory", Science, (2003) p. 337-339, vol. 300.

Sloat, B.R. et al., "Nasal immunization with the mixture of PA63, LF, and a PGA conjugate induced strong antibody response against all three antigens", FEMS Immunol Med Microbiol, (2008) p. 169-179, vol. 5.

Smith, K.M., et al., "In Vivo Generated Th1 Cells Can Migrate to B Cell Follicles to Support B Cell Responses", J. Immunol., (2004) p. 1640-1646, vol. 173.

Smith, T.F. and Waterman, M.S. "Comparison of Biosequences", Adv. Appl. Math, (1981) p. 482-489, vol. 2.

Sparwasser, T. et al., "Bacterial DNA and immunostimulatory CpG oligonucleotides trigger maturation and activation of murine dendritic cells", Eur. J. Immunol., (1998) p. 2045-2054, vol. 28.

Stephen, E.L. et al., "Effect of a nuclease-resistant derivative of polyriboinosinic-polyribocytidylic acid complex on yellow fever in rhesus monkeys (*Macaca mulatta*)", J Infect Dis, (1977) p. 122-126, vol. 136.

Stephen, E.L. et al., "Swine influenza virus vaccine: potentiation of antibody responses in rhesus monkeys", Science, (1977) p. 1289-1290, vol. 197.

Stern, P.L., "Immune control of human papillomavirus (HPV) associated anogenital disease and potential for vaccination", J. Clin. Virol., (2005) 32 Suppl. 1:S72-81.

Takeuchi, O. et al., "Cutting edge: role of toll-like receptor 1 in mediating immune response to microbial lipoproteins", The Journal of Immunology (2002) p. 10-14, ISSN 0022-1767, vol. 169.

Talmadge, J.E. et al., "Immunotherapeutic potential in murine tumor models of polyinosinic polycytidylic acid and poly-L-lysine solubilized by carboxymethylcellulose", Cancer Res., (1985) p. 1066-1072, vol. 45.

Teuten, A.J. et al., "Characterization of structural and folding properties of streptokinase by n.m.r. spectroscopy", Biochem. J., (1993) p. 313-319, vol. 290.

The National Wildlife Research Center, "Porcine Zona Pellucida Immunocontraception in Mammals," (Oct. 9, 2007), accessed online: <www.a- phis.usda.gov/ws/nwrc/pzp.htm>.

Tillman, B.W. et al., "Adenoviral vectors targeted to CD40 enhance the efficacy of dendritic cell-based vaccination against human papillomavirus 16-induced tumor cells in a murine model", Cancer Res., (2000) p. 5456-5463, vol. 60.

Tiwari, S. et al., "Gel core liposomes: an advanced carrier for improved vaccine delivery", J. Microencapsul., (Feb. 2009), p. 75-82, vol. 26, No. 1 (Abstract only).

Torréns, I. et al., "A mutant streptokinase lacking the C-terminal 42 amino acids is less immunogenic", Immunology Letters, (1999) p. 213-218, vol. 70.

Torréns, I. et al., "Immunotherapy with CTL peptide and VSSP eradicated established human papillomavirus (HPV) type 16 E7-expressing tumors", Vaccine, (2005) p. 5768-5774, vol. 23.

Trumpfheller, C. et al., "The microbial mimic poly IC induces durable and protective CD4+ T cell immunity together with a dendritic cell targeted vaccine", Proc Natl Acad Sci USA, (2008) p. 2574-2579, vol. 105.

Tsukui, T. et al., "Interleukin 2 production in vitro by peripheral lymphocytes in response to human papillomavirus-derived peptides: correlation with cervical pathology", Cancer Res., (1996) p. 3967-3974, vol. 56.

Van Oosterhout, A.J.M. et al., "Th1/Th2 paradigm: not seeing the forest for the trees?", Eur. Respir. J., (2005) p. 591-593, vol. 25.

Velders, M.P. et al., "Eradication of established tumors by vaccination with Venezuelan equine encephalitis virus replicon particles delivering human papillomavirus 16 E7 RNA", Cancer Res., (2001) p. 7861-7867, vol. 61.

Walboomers, J.M. et al., "Human papillomavirus is a necessary cause of invasive cervical cancer worldwide", J. Pathol., (1999) p. 12-19, vol. 189.

Wang, J.-C. et al., "Cutting edge: CD4+ T cell help can be essential for primary CD8+ T cell responses in vivo", J. Immunol., (2003) p. 6339-6343, vol. 171.

Weeratna, R.D. et al., "CpG DNA induces stronger immune responses with less toxicity than other adjuvants", Vaccine (2000) p. 1755-1762, vol. 18.

Wiesmuller, K.H. et al., "Peptide vaccines and peptide libraries", Biol. Chem., (Apr. 2001), p. 571-579, vol. 382.

Wilcox, R.A. et al., "Provision of antigen and CD137 signaling breaks immunological ignorance, promoting regression of poorly immunogenic tumors", J. Clin. Invest., (2002) p. 651-659, vol. 109.

Willard et al., Pregnancy detection and the effects of age, body weight, and previous reproductive performance on pregnancy status and weaning rates of farmed fallow deer (*Dana dama*), J. Animal Science, (1999) p. 32-38, vol. 77.

Yoneyama, M. et al., "The RNA helicase RIG-1 has an essential function in double-stranded RNA-induced innate antiviral responses", Nat Immunol, (2004) p. 730-737, vol. 5.

Zaks, K. et al., "Efficient immunization and cross-priming by vaccine adjuvants containing TLR3 or TLR9 agonists complexed to cationic liposomes", J. Immunol., (2006) p. 7335-7345, vol. 176.

Zauner, W. et al., "Defined synthetic vaccines", Biol. Chem., (2001) p. 581-595, vol. 382.

Zhu, X. et al. "Toll like receptor-3 ligand poly-ICLC promotes the efficacy of peripheral vaccinations with tumor antigen-derived peptide epitopes in murine CNS tumor models", J Transl. Med., (2007) vol. 5:10.

Zinkernagel, R.M., "On cross-priming of MHC class 1-specific CTL: rule or exception?", Eur. J. Immunol., (2002) p. 2385-2392, vol. 32.

Zur Hausen, H., "Papillomaviruses and cancer: from basic studies to clinical application", Nat. Rev. Cancer, (2002) p. 342-350, vol. 2.

International Search Report dated Dec. 19, 2008, International Application No. PCT/CA2008/001747.

International Search Report and Written Opinion issued in International Application No. PCT/CA2008/001678 dated Dec. 30, 2008.

Sabena Uddowla et al., "Effect of adjuvants and route of immunizations on the immune response to recombinant plague antigens", Vaccine, vol. 25, No. 47, 2007, pp. 7984-7993.

Beljanski et al., "Enhanced Influenza Virus-Like Particle Vaccination with a Structurally Optimized RIG-1 Agonist as Adjuvant", Journal of Virology, Oct. 2015, vol. 89, No. 20, pp. 10612-10624.

(56) References Cited

OTHER PUBLICATIONS

De Gregorio et al., "Alum adjuvanticity: Unraveling a century old mystery", European Journal of Immunology, 2008, vol. 38, pp. 2068-2071.
Fransen, Floris et al., "Agonists of Toll-Like Receptors 3, 4, 7, and 9 Are Candidates for Use as Adjuvants in an Outer Membrane Vaccine against Neisseria Meningitidis Serogroup B", Infection and Immunity, Dec. 2007, vol. 75, No. 12, pp. 5939-5946.
First Examination Report for POC/Application No. 7749/CHENP/2010 dated Dec. 5, 2017.
JP 2014-231396 Decision of Rejection and English Translation FP10-0388A dated Oct. 11, 2016.
JP 2014-231396 Decision to Dismiss Amendment and English Translation FP 10-0388A dated Oct. 11, 2016.
Dileo et al., "Lipid-Protamine-DNA-Mediated Antigen Delivery to Antigen-Presenting Ceils Results in Enhanced Anti-tumor Immune Responses", Molecular Therapy, vol. 7, No. 5, May 2003, pp. 640-648.
Compagnon et al., "Targeting of Poly(rl)-Poly(rC) by Fusogenic (F Protein) Immunoliposomes", Experimental Cell Research, vol. 260, pp. 333-338, 1992.
Supplementary European Search Report for related EP application No. EP 09 75 6985 dated Mar. 22, 2012.
Senior et al., "Stability of small unilamellar liposomes in serum and clearance from the circulation: The effect of the phospholipid and cholesterol components" Life Sciences, 1982, vol. 30, issue 24, pp. 2123-2136.
Marciani, "Vaccine Adjuvants: role and mechanisms of action in vaccine Immunogenicity" DDT, Oct. 2003, vol. 8, No. 26, pp. 934-943.
Joseph et al., "Liposomal immunostimulatory DNA sequence (ISS-ODN): an efficient parenteral and mucosal adjuvant for influenza and hepatitis B vaccines" Vaccine, 2002, vol. 20, pp. 3342-3354.
Aichinger et al., "Unique membrane-interacting properties of the immunostimulatory cationic peptide KLKL5KLK (KLK)" Cell Biology International, 2008, vol. 32, pp. 1449-1458.
Tafaghodi et al., "Nasal immunization studies using liposomes loaded with tetanus toxoid and CpG-ODN" Eur. J. Pham. Biopharm., 2006, 64, pp. 138-145.
Le Bon et al., "Type I Interferons Potently Enhance Humoral Immunity and Can Promote Isotype Switching by Stimulating Dendritic Cells in Vivo" Immunity, Apr. 2001, vol. 14, pp. 461-470.
Storni et al., "Immunity in response to particulate antigen-delivery systems" Advanced Drug Delivery Reviews, 2005, vol. 57, pp. 333-355.
Stanicova et al., "Amantadine: an antiviral and antiparkinsonian agent" Vet. Med.—Czech, 2001, 9-10, pp. 244-256.
Davis et al., "Liposomes as adjuvants with immunopurified tetanus toxoid: influence of liposomal characteristics" Immunology, 1987, 61, pp. 229-234.
Klinman et al., "Contribution of CpG Motifs to the Immunogenicity of DNA Vaccines", The Journal of Immunology, 1997, vol. 158, pp. 3635-3639.
Dass, "Liposome-Mediated Delivery of Oligodeoxynucleotides In Vivo", Drug Delivery, 2002, vol. 9, No. 3, pp. 169-180.
Evans et al., "Antigen Processing Defects in Cervical Carcinomas Limit the Presentation of a CTL Epitope from Human Papillomavirus 16 E6", The Journal of Immunology, 2001, vol. 167, pp. 5420-5428.
Tai et al., A Universal T Cell Vaccine Against Influenza A, The FASEB Journal, Apr. 2008, vol. 22., Issue S1, Abstract No. 853.11.
International Search Report and Written Opinion dated Sep. 2, 2009, International Application No. PCT/CA2009/000692.
PCT/CA2009/000692 International Preliminary Report on Patentability dated Dec. 6, 2010.
Conejero-Lara et al., "Thermal Stability of the Three Domains of Streptokinase Studied by Circular Dichroism and Nuclear Magnetic Resonance," Protein Science, vol. 5, pp. 2583-2591 (1996).
Dockrell and Kinghorn, "Imiquimod and resiquimod as novel immunomodulators," Journal of Antimicrobial Chemotherapy 48: 751-755 (2001).
Rechtsteiner et al., "Cutting Edge: Priming of CTL by transcutaneous peptide immunization with imiquimod," Journal of Immunology 174: 2476-2480 (2005).
Witt et al., "Phase I trial of an oral immunomodulator and interferon inducer in cancer patients," Cancer Research 53: 5176-5180 (1993).
Ninomiya et al., "Intranasal administration of a synthetic peptide vaccine encapsulated in liposome together with an anti-CD40 antibody induces protective immunity against influenza A virus in mice," Vaccine. 20(25-26): 3123-9 (2002).
Stone, "Newcastle Disease Oil Emulsion Vaccines Prepared with Animal, Vegetable, and Synthetic Oils", Avian Diseases 41:591-597, 1997.
European Search Report for European Patent Application No. EP 06790800.4 (dated Nov. 13, 2008).
Office Action for European Patent Application No. 06 790 800.4, dated Oct. 19, 2009.
Supplementary EP Search Report for related Application No. EP 08 80 0418 dated Jun. 21, 2012.
First Office Action regarding Canadian companion case 2,700,828, dated Oct. 2, 2014 (4 pages).
International Search Report for PCT/CA2006/001640 (dated Jan. 29, 2007).
Maes et al., "Potentiation of FMD vaccines with polycationic-nucleic acid complexes", Archives of Virology, 1977, vol. 55, No. 4, p. 275-285.
"Assessment and Harmonization of Laboratory Diagnostic Procedures Related to Human Papillomavirus Caccine Research and Development," Technical Meeting: Department of Vaccines and Biologicals, Heidelberg (2001 ).
DeLeo, "p53-Based Immunotherapy of Cancer," Critical Reviews in Immunology, 1998, vol. 18, pp. 29-35.
Richards et al., "Liposome-stabilized Oil-in-Water Emulsions as Adjuvants: Increased Emulsion Stability Promotes Induction of Cytotoxic T Lymphocytes Against an HIV Envelope Antigen," Immunology and Cell Biology, 2004, vol. 82, pp. 531-538.
Aucouturier et al., "Montanide ISA 720 and 51: a new generation of water in oil emulsions as adjuvants for human vaccines", Expert Rev. Vaccines, 2002, vol. 1, No. 1, pp. 111-118.
Sacco et al., "Effect of Varying Dosages and Adjuvants on Antibody Response in Squirrel Monkeys (*Saimiri sciureus*) Immunized with the Porcine Zona Pelludica Mr=55,000 Glycoprotein (ZP3)," Am. J. Reprod. Immunol. 21 :1-8 (1989).
Siskind et al., "Cell Selection by Antigen in the Immune Response," Adv. Immunol. 10:1-50 (1969).
Vierboom et al., "p53: A Target for T-Cell Mediated Immunotherapy," Peptide-Based Cancer Vaccines, W.M. Kast, Ed. Landes Bioscience, Georgetown, p. 40-55 (2000).
Ringleb (Dissertation 2004).
Office Action for U.S. Appl. No. 12/679,875, dated Nov. 20, 2012 (11 pages).
Final Office Action for U.S. Appl. No. 12/083,209, dated Oct. 27, 2015 (8 pages).
Office Action issued in U.S. Appl. No. 15/897,025 dated Apr. 10, 2018.
Office Action issued in U.S. Appl. No. 15/290,567 dated Oct. 2, 2017. (7 pages).
Office Action issued in U.S. Appl. No. 15/290,567 dated May 18, 2018. (15 pages).
Lingnau et al., "IC31 and IC30, novel types of vaccine adjuvant based on peptide delivery systems", Epert Rev. Vaccines, 2007, vol. 6, No. 5, pp. 741-746.
Biotechnological Drug Formulations—Basics and Applications; Edited by Xingguo Mei, Chemical Industry Press, 1st edition in Oct. 2004.

\* cited by examiner

1

USE OF LIPOSOMES IN A CARRIER COMPRISING A CONTINUOUS HYDROPHOBIC PHASE FOR DELIVERY OF POLYNUCLEOTIDES IN VIVO

CROSS-REFERENCE TO RELATED APPLICATIONS

This application is a continuation of U.S. patent application Ser. No. 15/290,567, filed Oct. 11, 2016, which is a continuation of U.S. patent application Ser. No. 12/679,875, filed Mar. 24, 2010 and issued as U.S. Patent No. 9,498,493, which is a National Stage of International Application No. PCT/CA2008/001678, filed Sep. 24, 2008, which claims the benefit of and priority to U.S. Provisional Patent Application No. 60/975,602 filed on Sep. 27, 2007 and U.S. Provisional Patent Application No. 61/061,303 filed Jun. 13, 2008, all of which are hereby incorporated by reference in their entirety.

FIELD OF THE INVENTION

The present application relates to the use of a composition comprising liposomes and a continuous hydrophobic phase as a vehicle for delivering polynucleotides in vivo.

BACKGROUND OF THE INVENTION

There has been much research into effective introduction of nucleic acids into target cells and tissues for use in e.g. gene therapy. Such nucleic acids may be e.g. sequences encoding a gene product or instead short sequences of nucleotides that correspond to the sense or antisense sequence of specific genes or their products and hence have a direct effect on the expression of these genes and/or their products.

There continue to exist problems in delivering the nucleic acids to the correct target site and to a sufficient number of target cells. Nucleic acids are subject to nuclease attack and are often unable to cross cell membranes. A wide variety of delivery methods have been proposed, including microinjection, scrape loading, and receptor-mediated endocytosis. Lipid-based carrier systems, including those involving use of liposomes, are frequently used to package the therapeutic nucleic acids. However, the use of liposomes may pose problems such as poor encapsulation efficacy and rapid clearance from circulation. There may also be problems in packaging enough nucleic without increasing the size of the liposome to the point where delivery to the target tissues is impaired. Accordingly, there exists a need to develop liposome-based delivery systems for targeting nucleic acids to the correct target tissue.

SUMMARY OF THE INVENTION

In one aspect, the invention provides a composition comprising: a carrier comprising a continuous phase of a hydrophobic substance; liposomes; and a polynucleotide.

In another aspect, the invention provides a method for delivering a polynucleotide to a subject, comprising administering the composition as described above to a subject.

Other aspects and features of the present invention will become apparent to those of ordinary skill in the art upon review of the following description of specific embodiments of the invention in conjunction with the accompanying figures.

BRIEF DESCRIPTION OF THE FIGURES

In the figures, which illustrate embodiments of the invention by way of example only.

DETAILED DESCRIPTION

Figure 1:
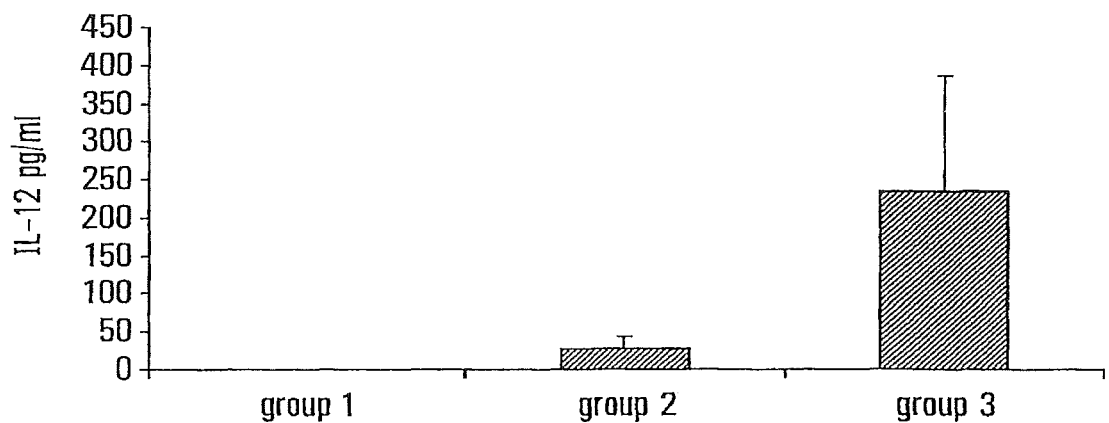
FIG. 1 illustrates IL-12 expression potential in cells isolated from lymph nodes 8 days post-injection.

The invention provides compositions useful for delivering a polynucleotide to a subject.

Polynucleotides

The use of polynucleotides as described herein refers specifically to polynucleotides that contain sequences that correspond largely to the sense or antisense sequence of specific genes or their products, and hence have a direct effect on the expression of these genes and/or their products. For example, the use of polynucleotides that contain gene coding sequences affects the transcription and/or translation of the genes of interest in cells that uptake such polynucleotides. Similarly, the use of RNA interference polynucleotides affects the expression of specific genes of interest by directly affecting the levels of mRNA in cells that uptake such nucleotides. This differs significantly from other polynucleotide-based molecules such as CpG and polyIC adjuvants, which do not act through the presence of gene specific sequences. Furthermore, polynucleotide-based adjuvants are believed to modulate an immune response in a non-specific manner, and their actions start at the site of vaccination where they interact with extracellular receptors to enhance the activity of immune cells in a non-specific manner. In some cases, polynucleotide-based adjuvants are internalized whereby they exert their effects by interacting with intracellular receptors, similarly leading to the activation of downstream pathways, and resulting collectively in the enhancement of immune cell activity to aid in the generation of an immune response. Such adjuvants do not directly affect the expression of specific genes that are being targeted by polynucleotide constructs as contemplated herein. Such adjuvants do not directly interact with the expression products of targeted genes, nor do they contain sequences that correspond to the sense or antisense sequence of targeted genes.

In one embodiment, the composition is useful for enhancing the expression of a polypeptide-encoding polynucleotide in vivo. In other embodiments; the polynucleotide may not encode a polypeptide, but may instead be e.g. a polynucleotide comprising or encoding an antisense RNA or other molecule that is not a polypeptide. In some embodiments, the compositions comprise a polynucleotide of interest, optionally operably linked to regulatory sequences suitable for directing protein expression from the polynucleotide (e.g. a promoter), liposomes, and a carrier comprising a continuous phase of a hydrophobic substance. Compositions of the invention were demonstrated to increase polypeptide expression from plasmid DNA, as measured by ELISA, in a murine model, relative to plasmid DNA suspended in phosphate buffered saline. Compositions of the invention were also demonstrated to increase polypeptide expression from plasmid DNA, as measured by immunofluorescence, in a murine model, relative to plasmid DNA suspended in phosphate buffered saline, Incomplete Freund's Adjuvant (IFA) or in liposomes with no oil.

As used herein the term "polynucleotide" encompasses a chain of nucleotides of any length (e.g. 9, 12, 18, 24, 30, 60, 150, 300, 600, 1500 or more nucleotides) or number of strands (e.g. single-stranded or double-stranded). Polynucleotides may be DNA (e.g. genomic DNA or cDNA) or RNA (e.g. mRNA) or combinations thereof. They may be naturally occurring or synthetic (e.g. chemically synthesized). It is contemplated that the polynucleotide may contain modifications of one or more nitrogenous bases, pentose sugars or phosphate groups in the nucleotide chain. Such modifications are well-known in the art and may be for the purpose of e.g. improving stability of the polynucleotide.

As used herein, the term "polypeptide" or "protein" means any chain of amino acids, regardless of length (e.g. 4, 6, 8, 10, 20, 50, 100, 200, 500 or more amino acids) or post-translational modification (e.g., glycosylation or phosphorylation). Both terms are used interchangeably.

The compositions of the invention are useful for delivering polynucleotides of all kinds to a subject in vivo. In some embodiments, the polynucleotide is not expressed as a protein in the subject, but rather encodes e.g. an antisense RNA, an interfering RNA, a catalytic RNA, or a ribozyme. In some embodiments, the polynucleotide encodes a polypeptide to be expressed in vivo in a subject. The invention is not limited to the expression of any particular type of polypeptide. The polypeptide may be, merely by way of illustrative examples, an antigen, an antibody or antibody fragment, an enzyme, a cytokine, a therapeutic protein, a chemokine, a regulatory protein, a structural protein, a chimeric protein, a nuclear protein, a transcription factor, a viral protein, a TLR protein, an interferon regulatory factor, an angiostatic or angiogenic protein, an apoptotic protein, an Fc gamma receptor, a hematopoietic protein, a tumor suppressor, a cytokine receptor, or a chemokine receptor.

Representative antigens include, without limitation: those derived from Cholera toxoid, tetanus toxoid, diphtheria toxoid, hepatitis B surface antigen, hemagglutinin, neuraminidase, influenza M protein, PfHRP2, pLDH, aldolase, MSP1, MSP2, AMA1, Der-p-1, Der-f-1, Adipophilin, AFP, AIM-2, ART-4, BAGE, alpha-fetoprotein, BCL-2, Bcr-Abl, BING-4, CEA, CPSF, CT, cyclin D1Ep-CAM, EphA2, EphA3, ELF-2, FGF-5, G250, Gonadotropin Releasing Hormone, HER-2, intestinal carboxyl esterase (iCE), IL13Ralpha2, MAGE-1, MAGE-2, MAGE-3, MART-1, MART-2, M-CSF, MDM-2, MMP-2, MUC-1, NY-EOS-1, MUM-1, MUM-2, MUM-3, p53, PBF, PRAME, PSA, PSMA, RAGE-1, RNF43, RU1, RU2AS, SART-1, SART-2, SART-3, SAGE-1, SCRN 1, SOX2, SOX10, STEAP1, surviving, Telomerase, TGFbetaRII, TRAG-3, TRP-1, TRP-2, TERT, or WT1; those derived from a virus, such as Cowpoxvirus, Vaccinia virus, Pseudocowpox virus, Human herpesvirus 1, Human herpesvirus 2, Cytomegalovirus, Human adenovirus A-F, Polyomavirus, Human papillomavirus, Parvovirus, Hepatitis A virus, Hepatitis B virus, Hepatitis C virus, Human immunodeficiency virus, Orthoreovirus, Rotavirus, Ebolavirus, parainfluenza virus, influenza A virus, influenza B virus, influenza C virus, Measles virus, Mumps virus, Rubella virus, Pneumovirus, Human respiratory syncytial virus, Rabies virus, California encephalitis virus, Japanese encephalitis virus, Hantaan virus, Lymphocytic choriomeningitis virus, Coronavirus, Enterovirus, Rhinovirus, Poliovirus, Norovirus, Flavivirus, Dengue virus, West Nile virus, Yellow fever virus and varicella; those derived from a bacterium, such as Anthrax, *Brucella, Candida, Chlamydia pneumoniae, Chlamydia psittaci, Cholera, Clostridium botulinum, Coccidioides immitis, Cryptococcus, Diphtheria, Escherichia coli* O157: H7, Enterohemorrhagic *Escherichia coli*, Enterotoxigenic *Escherichia coli, Haemophilus influenzae, Helicobacter pylori, Legionella, Leptospira, Listeria, Meningococcus, Mycoplasma pneumoniae, Mycobacterium, Pertussis, Pneumonia, Salmonella, Shigella, Staphylococcus, Streptococcus pneumoniae* and *Yersinia enterocolitica*; or those derived from a protozoa, e.g. *Plasmodium falciparum*.

RNA interference (RNAi) is a sequence specific post-transcriptional gene silencing mechanism, which is triggered by double-stranded RNA such as small (or short) interference RNA (siRNA) and single stranded intracellular RNA such as microRNA (miRNA), both of which can cause degradation of mRNAs homologous in sequence to siRNA or miRNA (Fire et al, 1998, Nature, 391:806-811; Montgomery et al, 1998, PNAS, 95:15502-15507; Elbashir et al, 2001, Nature, 411:494-498). RNAi is a conserved pathway common to plants and mammals that suppress expression of genes with complementary sequences (Hannon and Rossi, 2004, Nature, 431:371-378; Meister and Tuschl, 2004, Nature, 431, 343-349). RNAi was first observed in lower organisms, such as plants or nematodes. In these systems, long dsRNAs serve as effective triggers of RNAi. Long dsRNAs are not the actual triggers but are degraded by the endoribonuclease Dicer into small effector molecules called siRNAs. In mammals, Dicer processing occurs as a complex with the RNA-binding protein TRBP. The nascent siRNA associates with Dicer, TRBP, and Ago2 to form the RNA- Induced Silencing Complex (RISC) that mediates gene silencing (Chendrimada et al, 2005, Nature, 436:740-744). Once in RISC, one strand of the siRNA (the passenger strand) is degraded or discarded while the other strand (the guide strand) remains to direct sequence specificity of the silencing complex. The Ago2 component of RISC is a ribonuclease that cleaves a target RNA under direction of the guide strand.

Although long dsRNAs (several hundred bp) are commonly employed to trigger RNAi in C. elegans or D. melanogaster, these molecules will activate the innate immune system and trigger interferon (IFN) responses in higher organisms. RNAi can be performed in mammalian cells using short RNAs, which generally do not induce IFN responses. Many researchers today employ synthetic 21-mer RNA duplexes as their RNAi reagents, which mimic the natural siRNAs that result from Dicer processing of long substrate RNAs. An alternative approach is to use synthetic RNA duplexes that are greater than 21-mer in length, which are substrates for Dicer (Tuschl, T. 2002, Nature Biotechnology, 20:446).

Recently developed Dicer-substrate RNAs (DsiRNAs) are chemically synthesized RNA duplexes that have increased potency in RNA interference (Kim et al, 2005, Nat Biotechnol, 23:222-226). DsiRNAs are processed by Dicer into 21-mer siRNAs and designed so that cleavage results in a single, desired product. This is achieved through use of a novel asymmetric design where the RNA duplex has a single 2-base 3'-overhang on the AS strand and is blunt on the other end; the blunt end is modified with DNA bases. This design provides Dicer with a single favorable PAZ binding site that helps direct the cleavage reaction. Functional polarity is introduced by this processing event, which favors AS strand loading into RISC, and the increased potency of these reagents is thought to relate to linkage between Dicer processing and RISC loading (Rose et al, 2005, Nucleic Acids Res, 33:4140-4156). The Dicer-substrate approach can result in reagents having as much as 10-fold higher potency than traditional 21-mer siRNAs at the same site.

miRNA, first described in 1993 (Lee et al, 1993, Cell 75:843-854), are single-stranded RNA molecules of about 21-23 nucleotides in length, which regulate gene expression. miRNAs are encoded by genes that are transcribed from DNA but not translated into protein (non-coding RNA); instead they are processed from primary transcripts known as pri-miRNA to short stem-loop structures called pre-miRNA and finally to functional miRNA. Mature miRNA molecules are partially complementary to one or more messenger RNA (mRNA) molecules, and their main function is to downregulate gene expression. Although miRNA is generated within the cell and is highly conserved, it rarely has perfect complementarity with mRNA sequences. However, miRNA can affect protein translation and mRNA decay by binding to its imperfectly matched target sites on 3' UTR region of mRNA, which also requires Ago protein (not necessarily Ago2 as in seen in siRNA). Comparing and contrasting siRNA with miRNA shows that if siRNA hits an imperfect complementary target on 3 UTR, it behaves similar to microRNA, and if a miRNA hits a perfectly matched target on a mRNA, it can behave like an siRNA. Hence, although structurally different, both siRNA and miRNA might possess similar biological functions in the cells of host animal, with some differences in the mechanism of action.

Thus, RNAi molecules, siRNA and/or miRNA, provide a powerful tool for inhibiting endogenous gene expression and thereby could provide a means to effectively modulate biological responses. Studies have shown that RNAi can be induced in antigen presenting dendritic cells (DC) to polarize immune responses. By transfecting DC with synthetic siRNA specific for cytokine IL-12 p35 sub-unit, it was possible to inhibit bioactive IL-12 which subsequently led to Th2 polarization (Hill et al, J Immunology, 2003, 171:691). Similarly, modification of professional antigen presenting cells with siRNA in vivo has been used to enhance cancer vaccine potency (Kim et al, Cancer Research, 2005, 65:309-316). In this study, co-administration of DNA vaccine encoding human papilloma virus type 16 E7 with siRNA targeting key pro-apoptotic proteins Bac and Bax was shown to prolong the life span of antigen expressing DCs in the lymph nodes, enhancing antigen-specific CD8 T cell responses that had potent anti-tumor effects against an E7-expressing tumor model in vaccinated mice. Thus, there is a good prospect for the use of siRNA for silencing specific undesirable responses during effective vaccination against infectious/autoimmune diseases, cancer and during transplantation. Efficient delivery of siRNA to the intracellular compartment of cells of interest is critical for the success of such strategies, requiring the use of enhanced delivery formulations.

siRNA may be a naturally occurring or synthetic double stranded nucleotide (RNA) chain of varying length. siRNA can be duplexes, usually but not always limited to, 20 to 25-nt long that have 19 base pair central double stranded domain with terminal 2-base 3' overhangs. siRNA can be further modified chemically to enhance its in vivo efficacy, induce nuclease-resistance to prevent degradation and enhance stability. In this regard, the anti-sense strand may have either a free 5'-OH or 5'-phosphate terminus, the latter results in natural Dicer processing and represents the active form of the molecule. siRNA may have phosphorothioate or boranophosphate modification of the internucleoside linkage to improve nuclease stability and prolong life of the duplex when exposed to serum or other nuclease sources. siRNA may have modifications at 2'position, for example, 2'-O-methyl RNA residue incorporation to retain full potency compared with unmodified RNA, retaining stability in serum and significantly reducing the risk of potential IFN responses in the cell. siRNA may also have 2'-fluoro modification, which is usually incoLporated selectively at pyrimidine bases, to improve stability and potency.

siRNA and miRNA used as mediators of RNAi may be used as targets in, but not limited to, various infectious diseases, autoimmune/allergic diseases, heart diseases, metabolic disorders, solid tumors/cancers, hematological disorders/cancers.

In embodiments of the present invention, the polynucleotide in the composition may be a polynucleotide for use in RNAi, including, without limitation, an siRNA, an miRNA, a long dsRNA for cleavage by Dicer, or a DsiRNA, all as described above.

It has been demonstrated in the present invention that injection of IL-12 siRNA nucleotide sequences in vivo when formulated in a liposome/continuous hydrophobic carrier resulted in better inhibition of IL-12 protein expression induced by IL-12 plasmid than did IL-12 siRNA formulated in a PBS carrier. Similar results were achieved in experiments concerning inhibition of ovalbumin-induced IL-12 protein expression in cells isolated from lymph nodes, following injection of IL-12 siRNA. Again, IL-12 siRNA formulated in a liposome/continuous hydrophobic carrier gave superior results to IL-12 siRNA formulated in a PBS carrier.

The subject may be any subject to which it is desired to deliver a polynucleotide. The subject is preferably a vertebrate, such as a bird, fish or mammal, preferably a human.

The polynucleotide may delivered in various forms. In some embodiments, a naked polynucleotide may be used, either in linear form, or inserted into a plasmid, such as an expression plasmid. In other embodiments, a live vector such as a viral or bacterial vector may be used.

Depending on the nature of the polynucleotide and the intended use, one or more regulatory sequences that aid in transcription of DNA into RNA and/or translation of RNA into a polypeptide may be present. For example, if it is intended or not required that the polynucleotide be transcribed or translated, such regulatory sequences may be absent. In some instances, such as in the case of a polynucleotide that is a messenger RNA (mRNA) molecule, regulatory sequences relating to the transcription process (e.g. a promoter) are not required, and protein expression may be effected in the absence of a promoter. The skilled artisan can include suitable regulatory sequences as the circumstances require.

In some embodiments, the polynucleotide is present in an expression cassette, in which it is operably linked to regulatory sequences that will permit the polynucleotide to be expressed in the subject to which the composition of the invention is administered. The choice of expression cassette depends on the subject to which the composition is administered as well as the features desired for the expressed polypeptide.

Typically, an expression cassette includes a promoter that is functional in the subject and can be constitutive or inducible; a ribosome binding site; a start codon (ATG) if necessary; the polynucleotide encoding the polypeptide of interest; a stop codon; and optionally a 3' terminal region (translation and/or transcription terminator). Additional sequences such as a region encoding a signal peptide may be included. The polynucleotide encoding the polypeptide of interest may be homologous or heterologous to any of the other regulatory sequences in the expression cassette. Sequences to be expressed together with the polypeptide of interest, such as a signal peptide encoding region, are typically located adjacent to the polynucleotide encoding the protein to be expressed and placed in proper reading frame. The open reading frame constituted by the polynucleotide encoding the protein to be expressed solely or together with any other sequence to be expressed (e.g. the signal peptide), is placed under the control of the promoter so that transcription and translation occur in the subject to which the composition is administered.

Promoters suitable for expression of polynucleotides in a wide range of host systems are well-known in the art. Promoters suitable for expression of polynucleotides in mammmals include those that function constitutively, ubiquitously or tissue-specifically. Examples of non-tissue specific promoters include promoters of viral origin. Examples of viral promoters include Mouse Mammary Tumor Virus (MMTV) promoter, Human Immunodeficiency Virus Long Terminal Repeat (HIV LTR) promoter, Moloney virus, avian leukosis virus (ALV), Cytomegalovirus (CMV) immediate early promoter/enhancer, Rous Sarcoma Virus (RSV), adeno-associated virus (AAV) promoters; adenoviral promoters, and Epstein Barr Virus (EBV) promoters. Compatibility of viral promoters with certain polypeptides is a consideration since their combination may affect expression levels. It is possible to use synthetic promoter/enhancers to optimize expression (see e.g. US patent publication 2004/0171573).

An example of a tissue-specific promoter is the desmin promoter which drives expression in muscle cells (Li et al. 1989, Gene 78:243; Li & Paulin 1991, J. Biol. Chem. 266:6562 and Li & Paulin 1993, J. Biol. Chem. 268:10403). Other examples include artificial promoters such as a synthetic muscle specific promoter and a chimeric muscle-specific/CMV promoter (Li et al. 1999, Nat. Biotechnol. 17:241-245; Hagstrom et al. 2000, Blood 95:2536-2542).

Useful vectors are described in numerous publications, specifically WO 94/21797 and Hartikka et al. 1996, Human Gene Therapy 7:1205.

As noted above, the polynucleotide of interest, together with any necessary regulatory sequences, may be delivered naked, e.g. either alone or as part of a plasmid, or may be delivered in a viral or bacterial or bacterial vector.

Whether a plasmid-type vector, or a bacterial or viral vector is used, it may be desirable that the vector be unable to replicate or integrate substantially in the subject. Such vectors include those whose sequences are free of regions of substantial identity to the genome of the subject, as to minimize the risk of host-vector recombination. One way to do this is to use promoters not derived from the recipient genome to drive expression of the polypeptide of interest. For example, if the recipient is a mammal, the promoter is preferably non-mammalian derived though it should be able to function in mammalian cells, e.g. a viral promoter.

Viral vectors that may be used to deliver the polynucleotide include e.g. adenoviruses and poxviruses. Useful bacterial vectors include e.g. *Shigella, Salmonella, Vibrio cholerae, Lactobacillus*, Bacille bilié de Calmette-Guérin (BCG), and *Streptococcus*.

An example of an adenovirus vector, as well as a method for constructing an adenovirus vector capable of expressing a polynucleotide, is described in U.S. Pat. No. 4,920,209. Poxvirus vectors include vaccinia and canary pox virus, described in U.S. Pat. Nos. 4,722,848 and 5,364,773, respectively. Also see, e.g., Tartaglia et al. 1992, Virology 188:217 for a description of a vaccinia virus vector and Taylor et al. 1995, Vaccine 13:539 for a reference of a canary pox. Poxvirus vectors capable of expressing a polynucleotide of interest may be obtained by homologous recombination as described in Kieny et al. 1984, Nature 312:163, so that the polynucleotide is inserted in the viral genome under appropriate conditions for expression in mammalian cells.

With respect to bacterial vectors, non-toxicogenic *Vibrio cholerae* mutant strains that are useful for expressing a foreign polynucleotide in a host are known. Mekalanos et al. 1983, Nature 306:551 and U.S. Pat. No. 4,882,278 describe strains which have a substantial amount of the coding sequence of each of the two ctxA alleles deleted so that no functional *cholerae* toxin is produced. WO 92/11354 describes a strain in which the irgA locus is inactivated by mutation; this mutation can be combined in a single strain with ctxA mutations. WO 94/01533 describes a deletion mutant lacking functional ctxA and attRS1 DNA sequences. These mutant strains are genetically engineered to express heterologous proteins, as described in WO 94/19482.

Attenuated *Salmonella typhimurium* strains, genetically engineered for recombinant expression of heterologous proteins are described in Nakayama et al. 1988, Bio/Technology 6:693 and WO 92/11361.

Other bacterial strains which may be used as vectors to express a foreign protein in a subject are described for *Shigella flexneri* in High et al. 1992, EMBO 11:1991 and Sizemore et al. 1995, Science 270:299; for *Streptococcus gordonii* in Medaglini et al. 1995, Proc. Natl. Acad. Sci. USA. 92:6868; and for Bacille Calmette Guerin in Flynn 1994, Cell. Mol. Biol. 40 (suppl. I):31, WO 88/06626, WO 90/00594, WO 91/13157, WO 92/01796, and WO 92/21376.

In bacterial vectors, the polynucleotide of interest may be inserted into the bacterial genome or remain in a free state as part of a plasmid.

Liposomes

Liposomes are completely closed lipid bilayer membranes containing an entrapped aqueous volume. Liposomes may be unilamellar vesicles (possessing a single bilayer membrane) or multilamellar vesicles characterized by multimembrane bilayers, each bilayer may or may not be separated from the next by an aqueous layer. A general discussion of liposomes can be found in Gregoriadis G. *Immunol. Today,* 11:89-97, 1990; and Frezard, F., *Braz. J. Med. Bio. Res.,* 32:181-189, 1999. As used herein and in the claims, the term "liposomes" is intended to encompass all such vesicular structures as described above, including, without limitation, those described in the art as "niosomes", "transfersomes" and "virosomes".

Any liposomes may be used in this invention, including liposomes made from archaebacterial lipids. Any amphipathic lipid with at least one fatty acid chain containing at least 4 carbons, typically about 4 to 28 carbons in length may be used. The fatty acid chain may contain any number of saturated and/or unsaturated bonds. Amphipathic lipids contemplated may be phospholipids, sphingolipids, sphingomyelin, cerobrocides, gangliosides. Particularly useful liposomes use phospholipids and unesterified cholesterol in the liposome formulation. The cholesterol is used to stabilize the liposomes and any other compound that stabilizes liposomes may replace the cholesterol. Other liposome stabilizing compounds are known to those skilled in the art. For example, saturated phospholipids produce liposomes with higher transition temperatures indicating increased stability.

Phospholipids that are preferably used in the preparation of liposomes are those with at least one head group selected from the group consisting of phosphoglycerol, phosphoethanolamine, phosphoserine, phosphocholine and phosphoinositol. More preferred are liposomes that comprise lipids which are about 94-100% phosphatidylcholine. Such lipids are available commercially in the lecithin Phospholipon® 90 G (Phospholipid GmBH, Germany) or lecithin S100 (Lipoid GmBH, Germany). Other preferred phospholipids include cationic lipids such as 1,2-dioleoyl-3-trimethylammoniumpropane (DOTAP) and 1-[2-(oleoyloxy)ethyl]-2-oleyl-3-(2-hydroxyethyl)imidazolinium chloride (DOTIM).

When unesterified cholesterol is also used in liposome formulation, the cholesterol is usually used in an amount equivalent to about 10% of the amount of phospholipid. If a compound other than cholesterol is used to stabilize the liposomes, one skilled in the art can readily determine the amount needed in the composition.

Liposome compositions may be obtained, for example, by using natural lipids, synthetic lipids, sphingolipids, ether lipids, sterols, cardiolipin, cationic lipids and lipids modified with poly (ethylene glycol) and other polymers. Synthetic lipids may include the following fatty acid constituents: lauroyl, myristoyl, palmitoyl, stearoyl, arachidoyl, oleoyl, linoleoyl, erucoyl, or combinations of these fatty acids.

Carriers

The carrier of the composition comprises a continuous phase of a hydrophobic substance, preferably a liquid hydrophobic substance. The continuous phase may be an essentially pure hydrophobic substance or a mixture of hydrophobic substances. In addition, the carrier may be an emulsion of water in a hydrophobic substance or an emulsion of water in a mixture of hydrophobic substances, provided the hydrophobic substance constitutes the continuous phase. Further, in another embodiment, the carrier may function as an adjuvant.

Hydrophobic substances that are useful in the compositions as described herein are those that are pharmaceutically and/or immunologically acceptable. The carrier is preferably a liquid but certain hydrophobic substances that are not liquids at atmospheric temperature may be liquefied, for example by warming, and are also useful in this invention. In one embodiment, the hydrophobic carrier may be a PBS/FIA emulsion.

Oil or water-in-oil emulsions are particularly suitable carriers for use in the present invention. Oils should be pharmaceutically and/or immunologically acceptable. Preferred examples of oils are mineral oil such (especially light or low viscosity mineral oil), vegetable oil (e.g., soybean oil), nut oil (e.g., peanut oil). A low viscosity mineral oil such as Drakeol® 6VR is preferred in some embodiments. In a further embodiment, the oil is a mannide oleate in mineral oil solution, commercially available as Montanide® ISA 51. Animal fats and artificial hydrophobic polymeric materials, particularly those that are liquid at atmospheric temperature or that can be liquefied relatively easily, may also be used. Mixtures of different hydrophobic substances, such as mixtures that include one or more different oils, animal fats or artificial hydrophobic polymeric materials, may be used.

Additional Components

The composition may further comprise one or more additional components that may complement or enhance the function of the polypeptide to be expressed in the subject. For example, if the encoded polypeptide is a vaccine antigen, an additional component, such as an adjuvant, may be present. The term "adjuvant" refers to a compound or mixture that enhances the immune response to an antigen. An adjuvant can serve as a tissue depot that slowly releases the antigen and also as a lymphoid system activator that non-specifically enhances the immune response (Hood et al, Immunology, 2d ed., Benjamin/Cummings: Menlo Park, C. A., 1984; see Wood and Williams, In: Nicholson, Webster and May (eds.), Textbook of Influenza, Chapter 23, pp. 317-323). Often, a primary challenge with an antigen alone, in the absence of an adjuvant, will fail to elicit a humoral immune response. It should be noted that the polynucleotide of interest to be delivered to the subject may itself function as an adjuvant, or may encode a polypeptide that constitutes an adjuvant (e.g. IL-12, IFN-gamma, or Granulocyte-Macrophage Colony Stimulating Factor ("GMCSF")).

In some embodiments, suitable adjuvants include, but are not limited to, alum, other compounds of aluminum, *Bacillus* of Calmette and Guerin (BCG), TiterMax®, Ribi®, incomplete Freund's adjuvant (IFA), saponin, surface active substances such as lysolecithin, pluronic polyols, polyanions, peptides, *Corynebacterium parvum*, QS-21, and Freund's Complete Adjuvant (FCA), adjuvants of the TLR agonist family such as CpG, polyIC, falgellin, lipopeptides, peptidoglycans, imidazoquinolines, single stranded RNA, lipopolysaccharides (LPS), heat shock proteins (HSP), and ceramides and derivatives such as alpha Gal-cer. Suitable adjuvants also include cytokines or chemokines in their polypeptide or DNA coding forms such as, but not limited to, GM-CSF, TNF-alpha, IFN-gamma, IL-2, IL-12, IL-15, IL-21.

The amount of adjuvant used depends on the amount of antigen and on the type of adjuvant. One skilled in the art can readily determine the amount of adjuvant needed in a particular application.

A wide range of pharmaceutically acceptable adjuvants, excipients, etc. are known in the art and may be used in the compositions of the invention: See, for example, Remington's Pharmaceutical Sciences (Remington's Pharmaceutical Sciences, Mack Publishing Company, Easton, Pa., USA 1985) and The United States Pharmacopoeia: The National Formulary (USP 24 NF19) published in 1999.

If an additional component in the composition is a polypeptide, a polynucleotide encoding the additional polypeptide may instead be provided, in the same manner as for the polynucleotide encoding the polypeptide of primary interest. Such polypeptides could be expressed from the same or separate expression vectors, or could be expressed in the form of a fusion protein.

Formulation of Compositions

Methods for making liposomes are well known in the art: see, for example, Gregoriadis (1990) and Frezard (1999), both cited previously. Any suitable method for making liposomes may be used in the practice of the invention. Liposomes are typically prepared by hydrating the liposome components that will form the lipid bilayer (e.g. phospholipids and cholesterol) with an aqueous solution, which may be pure water or any other physiologically compatible solution such as saline, e.g. phosphate-buffered saline (PBS).

In an embodiment, a liposome component or mixture of liposome components, such as a phospholipid (e.g. Phospholipon® 90G) and cholesterol, may be solubilized in an organic solvent, such as a mixture of chloroform and methanol, followed by filtering (e.g. a PTFE 0.2 μm filter) and drying, e.g. by rotary evaporation, to remove the solvents.

Hydration of the resulting lipid mixture may be effected by e.g. injecting the lipid mixture into an aqueous solution or sonicating the lipid mixture and an aqueous solution. During formation of liposomes, the liposome components form single bilayers (unilamellar) or multiple bilayers (multilamellar) surrounding a volume of the aqueous solution with which the liposome components are hydrated.

In some embodiments, the liposomes are then dehydrated, such as by freeze-drying or lyophilization, and subsequently reconstituted with an aqueous solution.

The liposomes are combined with the carrier comprising a continuous hydrophobic phase. This can be done in a variety of ways.

If the carrier is essentially water-free, and is composed solely of a hydrophobic substance or a mixture of hydrophobic substances (e.g. use of a 100% mineral oil carrier), the liposomes may simply be mixed with the hydrophobic substance, or if there are multiple hydrophobic substances, mixed with any one or a combination of them.

If instead the carrier comprising a continuous phase of a hydrophobic substance contains a discontinuous aqueous phase, the carrier will typically take the form of an emulsion of the aqueous phase in the hydrophobic phase, such as a water-in-oil emulsion. Such compositions may contain an emulsifier to stabilize the emulsion and to promote an even distribution of the liposomes. In this regard, emulsifiers may be useful even if water-free carrier is used, for the purpose of promoting an even distribution of the liposomes in the carrier. Typical emulsifiers include mannide oleate (Arlacel™ A), lecithin, Tween™ 80, and Spans™ 20, 80, 83 and 85. Typically, the weight to volume ratio (w/v) of hydrophobic substance to emulsifier is in the range of about 5:1 to about 15:1 with a ratio of about 10:1 being preferred.

The liposomes may be added to the finished emulsion, or they may be present in either the aqueous phase or the hydrophobic phase prior to emulsification.

The polynucleotide to be expressed may be introduced at various different stages of the formulation process. In this section, the term "polynucleotide" includes the polynucleotide in naked form including in a plasmid such as an expression plasmid, or in a live vector such as a bacteria or virus.

More than one polynucleotide may be incorporated into the composition. For example, two or more polynucleotides encoding different proteins may be incorporated into the composition, or a polynucleotide encoding a protein may be present as well as a polynucleotide encoding an antisense RNA or interfering RNA. Proteins may be expressed as the fusion product of two different polynucleotides. More than one polynucleotide may be under the control of the same regulatory elements, e.g. two or more polynucleotides under transcriptional control of a single promoter.

In some embodiments, the polynucleotide is present in the aqueous solution used to hydrate the components that are used to form the lipid bilayers of the liposomes (e.g. phospholipid(s) and cholesterol). In this case, the polynucleotide will be encapsulated in the liposome, present in its aqueous interior. If the resulting liposomes are not washed or dried, such that there is residual aqueous solution present that is ultimately mixed with the carrier comprising a continuous phase of a hydrophobic substance, it is possible that additional polynucleotide may be present outside the liposomes in the final product. In a related technique, the polynucleotide may be mixed with the components used to form the lipid bilayers of the liposomes, prior to hydration with the aqueous solution.

In an alternative approach, the polynucleotide may instead be mixed with the carrier comprising a continuous phase of a hydrophobic substance, before, during, or after the carrier is combined with the liposomes. If the carrier is an emulsion, the polynucleotide may be mixed with either or both of the aqueous phase or hydrophobic phase prior to emulsification. Alternatively, the polynucleotide may be mixed with the carrier after emulsification.

The technique of combining the polynucleotide with the carrier may be used together with encapsulation of the polynucleotide in the liposomes as described above, such that polynucleotide is present both within the liposomes and in the carrier comprising a continuous phase of a hydrophobic substance.

Generally, the composition may comprise about 0.1 to 5 mg polynucleotide per ml of the composition and about 1 mg to 300 mg liposomes per ml of the composition.

If the composition contains one or more additional components (e.g. an adjuvant), the additional component(s) can be incorporated in the composition together with the polynucleotide at the same processing step, or separately, at a different processing step. For instance, the polynucleotide and the additional component may both be present in the aqueous solution used to hydrate the lipid bilayer-forming liposome components, such that both the polynucleotide and additional component become encapsulated in the liposomes. Alternatively, the polynucleotide may be encapsulated in the liposomes, and the additional component mixed with the carrier comprising a continuous phase of a hydrophobic substance. It will be appreciated that many such combinations are possible.

In some embodiments, the polynucleotide and the additional component may be in the form of a complex, in which they are in intimate contact at least prior to incorporation into the composition. Complexing may but need not necessarily involve a chemical linkage, such as covalent bonding.

The compositions as described herein may be formulated in a form that is suitable for oral, nasal, rectal or parenteral administration. Parenteral administration includes intravenous, intraperitoneal, intradermal, subcutaneous, intramuscular, transepithelial, intrapulmonary, intrathecal, and topical modes of administration. The preferred routes are intramuscular, subcutaneous and intradermal to achieve a depot effect. In practice, a depot effect is achieved when the therapeutic agent remains at the site of injection for more than about one hour.

The injection site may be anywhere close to, or directly into a lymph node, for example. Alternatively, the injection site may be directly into a spleen, a tumour or other diseased tissue. The volume that may be injected is within the professional judgment of the clinician. The volume depends on the injecting device used and the site of injection. When the injection is intramuscularly or subcutaneous, the injection volume may be about 2 mL. When needleless injection is used, the volume may be as low as 0.05 mL. The volume may be increased by injecting multiple sites.

Kits and Reagents

The present invention is optionally provided to a user as a kit. For example, a kit of the invention contains one or more of the compositions of the invention. The kit can further comprise one or more additional reagents, packaging material, containers for holding the components of the kit, and an instruction set or user manual detailing preferred methods of using the kit components for a desired purpose.

Uses

The invention finds application in any instance in which it is desired deliver a polynucleotide to a subject. Many such applications will be in the treatment or prevention of disease. Representative applications of the invention include cancer treatment and prevention, gene therapy, adjuvant therapy, infectious disease treatment and prevention, allergy treatment and prevention, autoimmune disease treatment and prevention, neuron-degenerative disease treatment, and artheriosclerosis treatment.

Prevention or treatment of disease includes obtaining beneficial or desired results, including clinical results. Beneficial or desired clinical results can include, but are not limited to, alleviation or amelioration of one or more symptoms or conditions, diminishment of extent of disease, stabilisation of the state of disease, prevention of development of disease, prevention of spread of disease, delay or slowing of disease progression, delay or slowing of disease onset, conferring protective immunity against a disease-causing agent and amelioration or palliation of the disease state. Prevention or treatment can also mean prolonging survival of a patient beyond that expected in the absence of treatment and can also mean inhibiting the progression of disease temporarily, although more preferably, it involves preventing the occurrence of disease such as by preventing infection in a subject.

The skilled artisan can determine suitable treatment regimes, routes of administration, dosages, etc., for any particular application in order to achieve the desired result. Factors that may be taken into account include, e.g.: the nature of a polypeptide to be expressed; the disease state to be prevented or treated; the age, physical condition, body weight, sex and diet of the subject; and other clinical factors.

The invention is further illustrated by the following non-limiting examples.

EXAMPLES

Example 1

In order to demonstrate the ability to enhance the expression of a protein-coding nucleotide sequence in vivo using a formulation comprising of liposomes and a continuous hydrophobic carrier, a model expression plasmid engineered with IL-12 complete coding sequence was selected. The IL-12 plasmid was formulated in liposome first, and the resulting IL-12 plasmid/liposome preparation was emulsified in a model water-in-oil emulsion with the continuous hydrophobic carrier consisting of mineral oil. In vivo expression was determined by examining the IL-12 expression potential in cells isolated from lymph node in the proximity of the injection site.

Pathogen free, female C57BL/6 mice, 6-8 weeks of age, were obtained from Charles River Laboratories (St Constant, Quebec, Canada) and were housed according to institutional guideline with water and food ad libitum, under filter controlled air circulation.

Murine IL-12 plasmid, pORF-mIL-12 was purchased from InvivoGen, San Diego, Calif., USA. The plasmid, supplied as lyophilized in GT100 *E. coli* bacteria transformed by pORF-mIL-12, was reconstituted in LB medium and streaked on an ampicillin-LB agar plate and incubated overnight at 37° C. Bacteria were grown from single colony in TB medium supplemented with ampicillin using. Plasmid DNA was purified from large scale bacterial cultures using endo-free Maxi- or Mega-prep kits (Qiagen, Mississauga, Ontario, Canada) to ensure complete removal of LPS.

Multilamellar liposomes were prepared by hydrating a 10:1 (W/W) mixture of dioleoyl phosphatidylcholine (DOPC) and cholesterol using phosphate buffered saline (PBS) containing IL-12 plasmid at a final concentration of 1 milligram/milliliter. Liposomes were then extruded through a 200 nm polycarbonate membrane using a manual extruder (Avanti lipids, Alabaster, Al, USA). The final liposome preparation was subsequently emulsified in Incomplete Freund's adjuvant (Sigma, Oakville, Ontario, Canada), a mineral oil based oil carrier, by mixing an equal volume of liposomes containing IL-12 plasmid and incomplete Freund's adjuvant.

Three groups of mice containing three mice each (n=3) were injected subcutaneously in the right flank above the base of the tail as follows: Group 1 was injected with phosphate buffered saline, Group 2 with 50 micrograms of IL-12 plasmid in PBS, and Group 3 with 50 micrograms of IL-12 plasmid formulated as described above in a liposome/continuous hydrophobic carrier. All injections were 100 microliters in volume. Draining lymph nodes from all mice were collected 8 days post-injection. Lymph nodes were dissected and single cell suspensions was cultured in vitro at a concentration of $2\times10^6$ cell/ml in RPMI medium supplemented with 10% FBS, penicillin/streptomycin, 2-ρ-mercaptoethanol and L-glutamine in 6 well plates for 48 h. Cell culture supernatants were collected and stored frozen in aliquots until used for IL-12 protein quantification.

Efficacy of IL-12 gene expression in the lymph nodes was determined by quantifying levels of IL-12 protein secreted into the cell culture supernatants. IL-12 protein quantification was performed by enzyme linked immunosorbent assay (ELISA), using a commercial IL-12 specific ELISA kit (Peptrotech, Rocky Hill, N.J., USA). Briefly, anti-IL-12 capture antibody was coated overnight on ELISA plates and samples and standard IL-12 were added. After thorough washes, biotinylated anti-IL-12 detection antibody was added and incubated for 2 h at room temperature and washed. Following incubation with Avidin-HRP conjugates and washes, ARTS liquid substrate (Sigma, St Louis, Mo.) was used for color development. Absorbances were read at 405 nm using a microtiter plate reader and IL-12 concentrations were extrapolated using a standard curve that was generated using IL-12 standards supplied in the kit.

IL-12 levels secreted by lymph node cells isolated from Groups 1-3 are shown in FIG. 1. Lymph node cells isolated from mice injected with PBS (Group 1) did not secrete detectable IL-12 protein into the culture supernatants. Low levels of IL-12 protein were secreted by lymph node cells isolated from mice injected with IL-12 plasmid in PBS. However, lymph nodes cells isolated from mice injected with IL-12 plasmid in a formulation comprising liposomes in a continuous hydrophobic carrier secreted a significantly higher level of IL-12, suggesting improved delivery of protein-coding nucleotide sequences in vivo and resulting in enhanced protein expression.

Example 2

Pathogen free, female C57BL/6 mice, 6-8 weeks of age, were obtained from Charles River Laboratories (St Constant, Quebec, Canada) and were housed according to institutional guideline with water and food ad libitum, under filter controlled air circulation.

Murine IL-12 plasmid, pORF-mIL-12 was purchased from InvivoGen, San Diego, Calif., USA. The plasmid, supplied as lyophilized in GT100 *E. coli* bacteria transformed by pORF-mIL-12, was reconstituted in LB medium and streaked on an ampicillin-LB agar plate and incubated overnight at 37° C. Bacteria were grown from single colony in TB medium supplemented with ampicillin using. Plasmid DNA was purified from large scale bacterial cultures using endo-free Maxi- or Mega-prep kits (Qiagen, Mississauga, Ontario, Canada) to ensure complete removal of LPS.

Multilamellar liposomes were prepared by hydrating a 10:1 (W/W) mixture of purified soy-derived mixture of phospholipids (phospholipid S100, provided by Lipoid GmbH) and cholesterol using phosphate buffered saline (PBS) containing IL-12 plasmid at a final concentration of 0.8 milligram/milliliter. Liposomes were then extruded through a 200 nm polycarbonate membrane using a manual extruder (Avanti lipids, Alabaster, Al, USA). The final liposome preparation was subsequently emulsified in Incomplete Freund's adjuvant (Sigma, Oakville, Ontario, Canada), a mineral oil based oil carrier, by mixing an equal volume of liposomes containing IL-12 plasmid and incomplete Freund's adjuvant. The final injected volume for each mouse was 100 microliters.

Six groups of mice containing five mice each (n=5) were injected subcutaneously in the right flank above the base of the tail as follows: Group 1 mice were injected with 40 micrograms of IL-12 plasmid in PBS, Group 2 mice with 40 micrograms of IL-12 plasmid formulated as described above in a liposome/continuous hydrophobic carrier, Group 3 mice with 40 micrograms of IL-12 plasmid formulated in a continuous hydrophobic carrier (incomplete Freund's adjuvant water-in-oil emulsion) without liposomes, Group 4 mice with 40 micrograms of IL-12 plasmid formulated in liposomes as described above but without a continuous hydrophobic carrier, Group 5 mice with a control formulation consisting of liposome/continuous hydrophobic carrier without IL-12 plasmid, and Group 6 mice remained untreated. All injections were 100 microliters in volume. Draining lymph nodes from all mice were collected B days post-injection. Lymph nodes were dissected and single cell suspensions was cultured in vitro at a concentration of 2×106 cell/ml in RPMI medium supplemented with 10% FBS, penicillin/streptomycin, 2-β-mercaptoethanol and L-glutamine in 6 well plates for 48 h. Cell culture supernatants were collected and stored frozen in aliquots until used for IL-12 protein quantification.

Efficacy of IL-12 gene expression in the lymph nodes was determined by quantifying levels of IL-12 protein secreted into the cell culture supernatants. IL-12 protein quantification was performed by enzyme linked immunosorbent assay (ELISA), using a commercial IL-12 specific ELISA kit (Peptrotech, Rocky Hill, N.J., USA). Briefly, anti-IL-12 capture antibody was coated overnight on ELISA plates and samples and standard IL-12 were added. After thorough washes, biotinylated anti-IL-12 detection antibody was added and incubated for 2 h at room temperature and washed. Following incubation with Avidin-HRP conjugates and washes, ABTS liquid substrate (Sigma, St Louis, Mo.) was used for color development. Absorbances were read at 405 nm using a microtiter plate reader and IL-12 Concentrations were extrapolated using a standard curve that was generated using IL-12 standards supplied in the kit.

Figure 2:
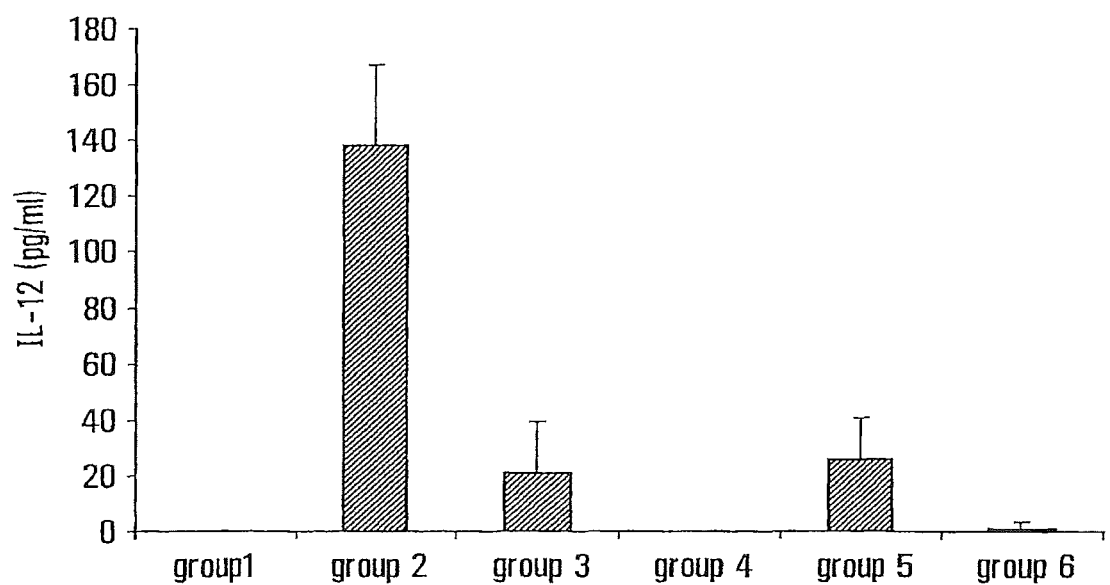
FIG. 2 illustrates IL-12 expression potential in cells isolated from lymph nodes 8 days post-injection. IL-12 protein levels detected from each group of mice were averaged.

IL-12 levels secreted by lymph node cells isolated from Groups 1-6 are shown in FIG. 2. Lymph node cells isolated from mice injected with IL-12 plasmid in PBS (Group 1) did not secrete detectable IL-12 protein into the culture supernatants. However, lymph nodes cells isolated from mice injected with IL-12 plasmid in a formulation comprising liposomes in a continuous hydrophobic carrier (Group 2) secreted a considerably higher level of IL-12. Lymph nodes cells isolated from mice from Group 3, Group 5 and Group 6 secreted significantly lower levels of IL-12 protein and lymph nodes cells isolated from mice from Group 4 did not secrete detectable IL-12 protein into the culture supernatants. In this experiment, superior IL-12 protein expression was achieved using a liposome/hydrophobic carrier formulation relative to formulations lacking either or both of liposomes and the continuous hydrophobic carrier.

Example 3

In order to demonstrate the ability to enhance the expression of a protein-coding nucleotide sequence in vivo using a formulation comprising of liposomes and a continuous hydrophobic carrier, a model expression plasmid engineered with green fluorescent protein (GFP) complete coding sequence was selected. The GFP plasmid was formulated in liposome first, and the resulting GFP plasmid/liposome preparation was emulsified in a model water-in-oil emulsion with the continuous hydrophobic carrier consisting of mineral oil. In vivo uptake and expression was determined by examining the GFP expression potential in cells isolated from lymph node in the proximity of the injection site.

Pathogen free, female C57BL/6 mice, 6-8 weeks of age, were obtained from Charles River Laboratories (St Constant, Quebec, Canada) and were housed according to institutional guideline with water and food ad libitum, under filter controlled air circulation.

Synthetic GFP plasmid, pMOD-GFPSh (catalog name, pmod-zgfpsh) was purchased from InvivoGen, San Diego, Calif., USA. The plasmid was transformed into XL1 strain of *E. coli* bacteria, grown in LB medium and streaked on an ampicillin-LB agar plate and incubated overnight at 37° C. Bacteria were grown from single colony in TB medium supplemented with ampicillin. Plasmid DNA was purified from large scale bacterial cultures using endo-free Maxi- or Mega-prep kits (Qiagen, Mississauga, Ontario, Canada) to ensure complete removal of LPS.

Multilamellar liposomes were prepared by hydrating a 10:1 (W/W) mixture of purified soy-derived mixture of phospholipids (phospholipid S100, provided by Lipoid GmbH) and cholesterol using phosphate buffered saline (PBS) containing GFP plasmid at a final concentration of 0.8 milligram/milliliter. Liposomes were then extruded through a 200 nm polycarbonate membrane using a manual extruder (Avanti lipids, Alabaster, Al, USA). The final liposome preparation was subsequently emulsified in Incomplete Freund's adjuvant (Sigma, Oakville, Ontario, Canada), a mineral oil based oil carrier, by mixing an equal volume of liposomes containing GFP plasmid and incomplete Freund's adjuvant. The final injected volume for each mouse was 100 microliters which delivered 40 micrograms plasmid per dose per mouse.

Six groups of mice containing four mice each (n=4) were injected subcutaneously in the right flank above the base of the tail as follows: Group 1 mice were injected with 40 micrograms of GFP plasmid in PBS, Group 2 mice with 40 micrograms of GFP plasmid formulated as described above in a liposome/continuous hydrophobic carrier, Group 3 mice with 40 micrograms of GFP plasmid formulated in a continuous hydrophobic carrier (incomplete Freund's adjuvant water-in-oil emulsion) without liposomes, Group 4 mice with 40 micrograms of GFP plasmid formulated in liposomes as described above but without a continuous hydrophobic carrier, Group 5 mice with a control formulation consisting of liposome/continuous hydrophobic carrier without GFP plasmid, and Group 6 mice remained untreated. All injections were 100 microliters in volume. Draining lymph node from all mice were collected 8 days post-injection. Lymph nodes were dissected and single cell suspensions was prepared. Efficacy of GFP gene expression in the lymph nodes was determined by two color immunofluorescence staining for detecting GFP-positive cells. Cells were stained with phycoerythrin-conjugated CD11b and CD11c antibodies for identifying antigen presenting cells in channel FL2 along with GFP detection in channel FL1. Samples were run through a flow cytometer (FACSCalibur, BD Biosciences, San Jose, Calif.). At least $3 \times 10^5$ events were collected for each sample to enhance the accuracy of detection of GFP positive cells.

Figure 3:
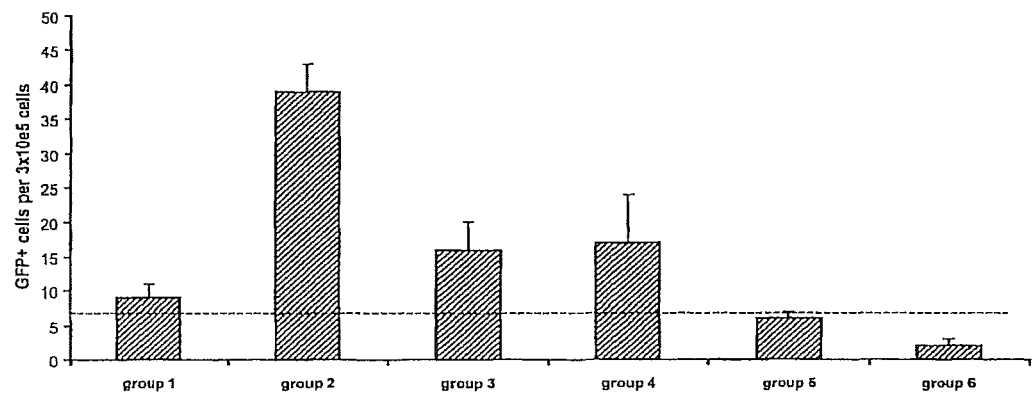
FIG. 3 illustrates green fluorescent protein (GFP) expression potential in cells isolated from lymph nodes 8 days post-injection. Lymph node cells from animals of Group 1 (GFP in PBS), Group 2 (GFP/liposome/hydrophobic carrier), Group 3 (GFP/hydrophobic carrier) and Group 4 (GFP/liposome) contained detectable GFP expressing cells above background fluorescence represented by a horizontal line. Background fluorescence was estimated using lymph node cell fluorescence counts from control animals of Group 5 (liposome/hydrophobic carrier, no GFP), and Group 6 (untreated mice). P values were calculated using the student T test.
Figure 4:
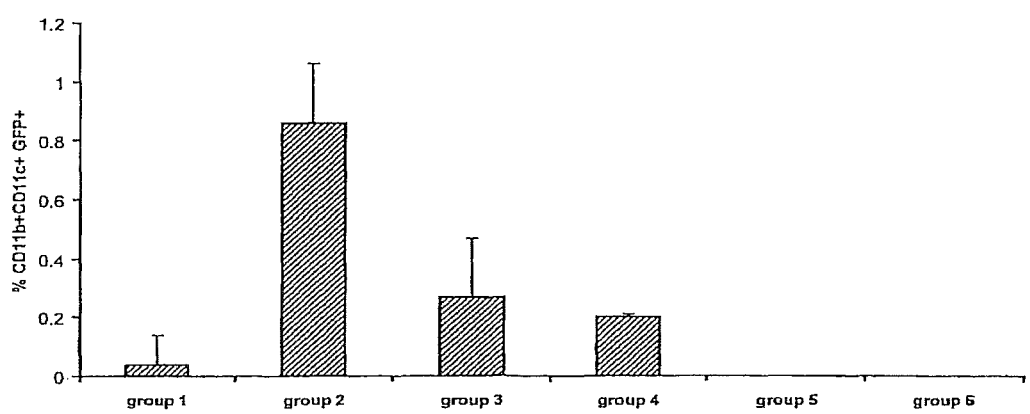
FIG. 4 illustrates CD11b/CD11c positive lymph node cells showing GFP expression at 8 days post-vaccination. Data presented in FIG. 1 was re-analyzed to compare the number of CD11b/CD11c and GFP positive cells in lymph nodes from animals of Groups 1-6 (described in FIG. 1). The number of CD11b/CD11c positive, GFP positive cells was calculated as a percentage of total lymph node cells.

Number of lymph node cells isolated from Group 1 to Group 6, expressing GFP (and thus are positively identified in flow cytometric analysis), are shown in FIG. 3. Lymph nodes isolated from mice injected with GFP plasmid in PBS (Group 1) showed low level of GFP protein expressing cells (<10). However, lymph nodes isolated from mice injected with GFP plasmid in a formulation comprising liposomes in a continuous hydrophobic carrier (Group 2) showed almost four-fold increase in GFP positive cells. Further, lymph nodes cells isolated from mice from Group 3 and Group 4 showed significantly lower number of GFP protein expressing cells compared to mice in Group 2. Among mice in Group 5 and Group 6, minimal fluorescence was detected which was attributed to background auto-fluorescence events as these mice did not receive GFP plasmid injections. Moreover, the majority of GFP positive cells were detected within the population of CD11b/CD110 positive lymph node cells. The results of a re-analysis of lymph node cells targeting specifically cells that are CD11b/CD11c and GFP double positive correlate with the finding presented in FIG. 3, with at least a 4 fold increase in GFP expression in CD11b/CD11c positive cells from Group 2 (FIG. 4). This re-analysis also confirmed that no specific fluorescence can be detected in lymph node cells from control Groups 5 and 6. This observation confirmed the specificity of GFP positive cell detection in this experiment. Thus, in the present experiment, superior GFP plasmid uptake and protein expression was achieved using a liposome/hydrophobic carrier formulation relative to formulations lacking either or both of liposomes and the continuous hydrophobic carrier.

Example 4

In order to demonstrate the ability to inhibit the expression of a protein-coding nucleotide sequence in vivo by siRNA against given protein-coding nucleotide sequence, using a formulation comprising of liposomes and a continuous hydrophobic carrier, a model expression plasmid engineered with IL-12 complete coding sequence and siRNA sequence for IL-12 was selected. The IL-12 plasmid was formulated in liposome first, and the resulting IL-12 plasmid/liposome preparation was emulsified in a model water-in-oil emulsion with the continuous hydrophobic carrier consisting of mineral oil. One day before IL-12 plasmid injection, siRNA was injected in either PBS or in liposome/water-in oil emulsion with the continuous hydrophobic carrier consisting of mineral oil. In vivo functional activity of siRNA was determined by examining the IL-12 expression potential in cells isolated from lymph node in the proximity of the injection site.

Pathogen free, female C57BL/6 mice, 6-8 weeks of age, were obtained from Charles River Laboratories (St Constant, Quebec, Canada) and were housed according to institutional guideline with water and food ad libitum, under filter controlled air circulation.

Murine IL-12 plasmid, pORF-mIL-12 was purchased from InvivoGen, San Diego, Calif., USA. The plasmid, supplied as lyophilized in GT100 *E. coli* bacteria transformed by pORF-mIL-12, was reconstituted in LB medium and streaked on an ampicillin-LB agar plate and incubated overnight at 37° C. Bacteria were grown from single colony in TB medium supplemented with ampicillin. Plasmid DNA was purified from large scale bacterial cultures using endo-free Maxi- or Mega-prep kits (Qiagen, Mississauga, Ontario, Canada) to ensure complete removal of LPS.

siRNA against murine IL-12 was purchased from Ambion Applied Biosystems, Austin, Tex., USA. This lyophilized product was >95% pure by analytical HPLC and contained less than 10EU of endotoxin by LAL assay. siRNA was dissolved in sterile phosphate buffered saline (PBS) before formulating for injection.

Multilamellar liposomes were prepared by hydrating a 10:1 (W/W) mixture of dioleoyl phosphatidylcholine (DOPC) and cholesterol using phosphate buffered saline (PBS) containing IL-12 plasmid at a final concentration of 1.6 milligram/milliliter. Liposomes were then extruded through a 200 nm polycarbonate membrane using a manual extruder (Avanti lipids, Alabaster, Al, USA). For every 500 microliters of a liposome/IL12 suspension, an equal volume of a mineral oil carrier (Montanide™ ISA 51, Seppic, France) was added to form a water-in-oil emulsion with the liposome suspension contained in the water phase of the emulsion and the oil forming the continuous phase, acting as a hydrophobic carrier.

In order to induce effective levels of IL-12 expression, three groups of mice containing three mice each (n=3) were all injected subcutaneously in the right flank above the base of the tail on day-0 with 40 micrograms of IL-12 plasmid formulated as described above in a liposome/continuous hydrophobic carrier in 50 microliters volume. Additionally, on day minus 1, Group 1 mice were injected with vehicle only, Group 2 mice were injected with 40 micrograms IL-12 siRNA in PBS and Group 3 mice were given 40 micrograms IL-12 siRNA in a liposome/continuous hydrophobic carrier, similar to the formulation used to deliver plasmid IL-12. All injections were given subcutaneously in the right flank above the base of the tail in 50 microlitre volume.

Draining lymph nodes from all injected mice and corresponding lymph nodes from three naïve mice (Group 4) were collected 8 days post-injection. Lymph nodes were dissected and single cell suspensions was cultured in vitro at a concentration of $2 \times 10^6$ cell/ml in RPMI medium supplemented with 10% FBS, penicillin/streptomycin, 2-β-mercaptoethanol and L-glutamine in 24 well plates for 48 h. Cell culture supernatants were collected and stored frozen in aliquots until used for IL-12 protein quantification.

Efficacy of siRNA injected in various formulations was determined by measuring the extent of inhibition in plasmid IL-12 induced IL-12 protein expression by lymph node cells. IL-12 protein quantification in cell culture supernatant was performed by enzyme linked immunosorbent assay (ELISA), using a commercial IL-12 specific ELISA kit (Peptrotech, Rocky Hill, N.J., USA). Briefly, anti-IL-12 capture antibody was coated overnight on ELISA plates and samples and standard IL-12 were added. After thorough washes, biotinylated anti-IL-12 detection antibody was added and incubated for 2 h at room temperature and washed. Following incubation with Avidin-HRP conjugates and washes, ABTS liquid substrate (Sigma, St Louis, Mo.) was used for color development. Absorbances were read at 405 nm using a microtiter plate reader and IL-12 concentrations were extrapolated using a standard curve that was generated using IL-12 standards supplied in the kit.

Figure 5:
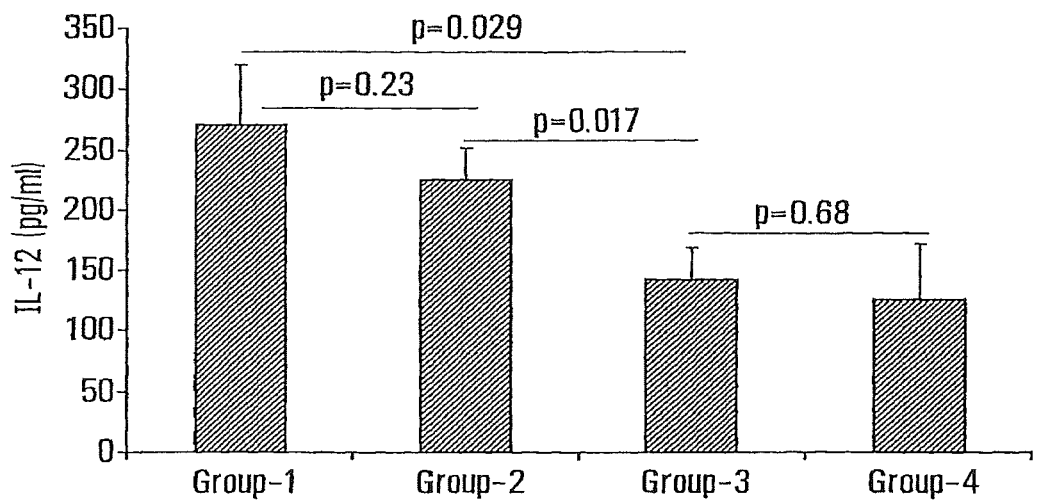
FIG. 5 illustrates inhibition of plasmid IL-12 induced IL-12 protein expression in cells isolated from lymph nodes, following injection of IL-12 siRNA. IL-12 protein levels detected from each group of mice were averaged. Lymph node cells are from Group 1 (pORF-mIL12 plasmid alone, no siRNA), Group 2 (pORF-mIL12 plasmid, IL12-siRNA in PBS), Group 3 (pORF-mIL12 plasmid, IL12-siRNA in liposome/hydrophobic carrier) and Group 4 (untreated, naïve mice). p-values were calculated using Students t test.

IL-12 levels secreted by lymph node cells isolated from Groups 1-4 are shown in FIG. 5. Lymph node cells isolated from mice injected with IL-12 plasmid alone, but not siRNA against IL-12 (Group 1), secreted 270.4 picograms per millilitre of IL-12 into the culture supernatants. In Group 2 mice, injected with IL-12 siRNA in PBS, no significant inhibition in IL-12 protein secretion was observed. In contrast, when siRNA was delivered in liposome/continuous hydrophobic barrier, marked decrease in secreted IL-12 was observed, which was as low as that observed with naïve mice. Moreover, lymph node cells from mice in Group 3 secreted significantly lower IL-12 compared to mice in Group 2 that received siRNA in PBS. This demonstrated an improved delivery of siRNA nucleotide sequences in vivo when injected in a liposome/continuous hydrophobic carrier that resulted in better inhibition of IL-12 protein expression induced by IL-12 plasmid.

Example 5

As a further example, to test the ability of IL-12 siRNA delivered in a liposome/continuous hydrophobic carrier to inhibit IL-12 secretion, ovalbumin antigen in complete Freund's adjuvant (CFA) was used to induce IL-12 secretion by lymph node cells. Protein antigen ovalbumin has been previously shown to induce IL-12 cytokine secretion in mice (Yotsumoto et al, 2007, Vaccine, 25:5256-5262), which could be inhibited using siRNA specific for IL-12 p35 (Hill et al, Journal of Immunology, 2003, 171:691; Ichim et al, Journal of Translational Medicine, 2006, 4:2, 1-11). In this example, mice injected with Ovalbumin in CFA subcutaneously were injected with IL-12 siRNA subcutaneously (either in PBS or in liposome/continuous hydrophobic carrier) one day before or one day after ovalbumin injection.

Pathogen free, female C57BL/6 mice, 6-8 weeks of age, were obtained from Charles River Laboratories (St Constant, Quebec, Canada) and were housed according to institutional guideline with water and food ad libitum, under filter controlled air circulation.

Mice were immunized subcutaneously in the right flank above the base of the tail with 5 micrograms of ovalbumin emulsified in CFA (Difco Laboratories, Detroit, Mich.) in 50 microlitre volume.

Multilamellar liposomes were prepared by hydrating a 10:1 (W/W) mixture of purified soy-derived mixture of phospholipids (phospholipid S100, provided by Lipoid GmbH) and cholesterol using phosphate buffered saline (PBS) containing IL-12 siRNA at a final concentration of 1.6 milligram/milliliter. Liposomes were then extruded through a 200 nm polycarbonate membrane using a manual extruder (Avanti lipids, Alabaster, Al, USA). For every 500 microliters of a liposome/IL12-siRNA suspension, an equal volume of a mineral oil carrier (Montanide™ ISA 51, Seppic, France) was added to form a water-in-oil emulsion with the liposome suspension contained in the water phase of the emulsion and the oil forming the continuous phase, acting as a hydrophobic carrier.

Five groups of mice (n=4) were all immunized subcutaneously on day-0 with ovalbumin formulated in complete Freund's adjuvant (CFA), and each group treated subcutaneously in the right flank above the base of the tail as follows: Group 1 mice were untreated, Group 2 mice with 40 micrograms of IL-12 siRNA in PBS on day minus one, Group 3 with siRNA formulated as described above in a liposome/continuous hydrophobic carrier on day minus one, Group 4 with siRNA in PBS on day plus one and Group 5 with siRNA in liposome/continuous hydrophobic carrier on day plus one, while Group 6 consisted of non-vaccinated and untreated naïve mice. All injections were 50 microliters in volume. Draining lymph nodes from all mice were collected 8 days post-ovalbumin injection. Lymph nodes were dissected and single cell suspensions was cultured in vitro at a concentration of $2 \times 10^6$ cell/ml in RPMI medium supplemented with 10% FBS, penicillin/streptomycin, 2-β-mercaptoethanol and L-glutamine in 24 well plates for 48 h. Cell culture supernatants were collected and stored frozen in aliquots until used for IL-12 protein quantification.

Efficacy of siRNA injected in two different formulations was determined by measuring the extent of inhibition in ovalbumin-induced IL-12 protein expression by lymph node cells. IL-12 protein quantification was performed by enzyme linked immunosorbent assay (ELISA), using a commercial IL-12 specific ELISA kit (Peptrotech, Rocky Hill, N.J., USA). Briefly, anti-IL-12 capture antibody was coated overnight on ELISA plates and samples and standard IL-12 were added. After thorough washes, biotinylated anti-IL-12 detection antibody was added and incubated for 2 h at room temperature and washed. Following incubation with Avidin-HRP conjugates and washes, ABTS liquid substrate (Sigma, St Louis, Mo.) was used for color development. Absorbances were read at 405 nm using a microtiter plate reader and IL-12 concentrations were extrapolated using a standard curve that was generated using IL-12 standards supplied in the kit.

Figure 6:
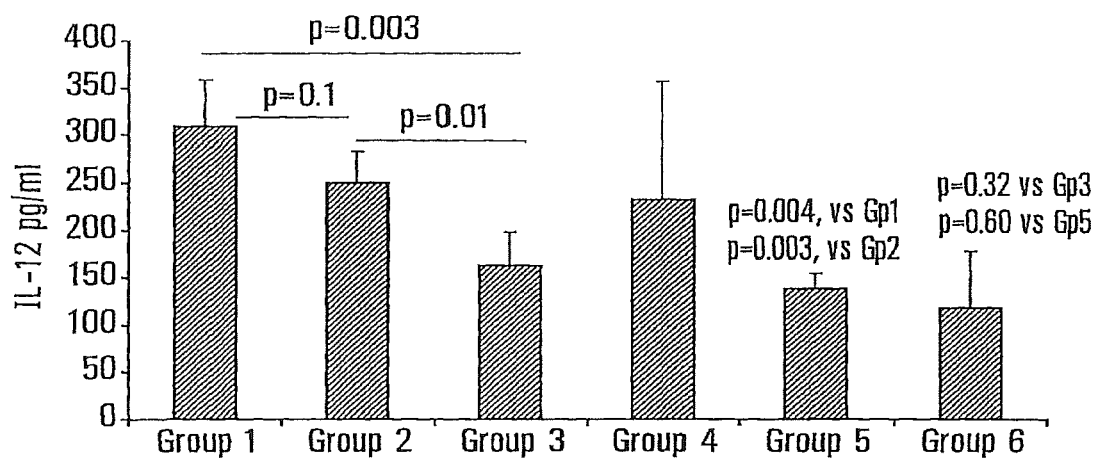
FIG. 6 illustrates inhibition of ovalbumin-induced IL-12 protein expression in cells isolated from lymph nodes, following injection of IL-12 siRNA. IL-12 protein levels detected from each group of mice were averaged. Lymph node cells are from Group 1 (ovalbumin in CFA on day-0, no siRNA), Group 2 (ovalbumin in CFA, IL12-siRNA in PBS, day minus 1), Group 3 (ovalbumin in CFA, IL12-siRNA in liposome/hydrophobic carrier, day minus 1), Group 4 (ovalbumin in CFA, IL12-siRNA in PBS, day plus 1), Group 5 (ovalbumin in CFA, IL12-siRNA in liposome/hydrophobic carrier, day plus 1) and Group 6 (untreated naïve mice). p-values were calculated using Students t test.

IL-12 levels secreted by lymph node cells isolated from Groups 1-6 are shown in FIG. 6. Lymph node cells isolated from mice in Group 1, which did not receive siRNA injection against IL-12, secreted more than 300 picograms per millilitre of IL-12 into the culture supernatants. In Group 2 mice, injected with IL-12 siRNA in PBS on day minus one or in Group 4 mice injected with IL-12 siRNA in PBS on day plus one relative to ovalbumin immunization, no significant inhibition in IL-12 protein secretion was observed. In contrast, when siRNA was delivered in liposome/continuous hydrophobic barrier either on day minus one (Group 3) or on plus one (Group 5), marked decrease in secreted IL-12 was observed (p=0.003 and p=0.004 respectively), which was as low as that observed with lymph node cells from naïve mice. Moreover, lymph node cells from mice in Group 3 and Group 5 secreted significantly lower IL-12 compared to mice in Group 2 and Group 4 that received siRNA in PBS. This shows an effective and improved delivery of siRNA nucleotide sequences in vivo when injected in a liposome/continuous hydrophobic carrier that resulted in complete inhibition of IL-12 protein expression induced by ovalbumin antigen.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

As used in this specification and the appended claims, the singular forms "a," "an," and "the" include plural reference unless the context clearly dictates otherwise. Unless defined otherwise all technical and scientific terms used herein have the same meaning as commonly understood to one of ordinary skill in the art to which this invention belongs.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

The invention claimed is:

1. An injectable composition comprising:
   a carrier comprising a continuous phase of oil;
   liposomes comprising a saturated or unsaturated phospholipid; and
   a polynucleotide encapsulated within said liposomes, said polynucleotide encoding a polypeptide and capable of being expressed in mammalian cells,
   wherein said carrier and said liposomes are present in a ratio of 1:1 by volume.

2. The composition according to claim 1, wherein the composition is a water-in-oil emulsion.

3. The composition according to claim 1, wherein said carrier is free of water.

4. The composition according to claim 1, wherein said oil comprises a natural oil, a synthetic oil or a combination thereof.

5. The composition according to claim 1, wherein said liposomes comprise cholesterol, dioleoyl phosphatidylcholine (DOPC), phosphoglycerol, phosphoethanolamine, phosphoserine, phosphocholine, phosphoinositol, phosphatidylcholine, lecithin, phosphatidylcholine and ascorbyl palmitate, 1,2-dioleoyl-3-trimethylammonium-propane (DOTAP),1-[2-(oleoyloxy)ethyl]-2-oleyl-3-(2-hydroxyethyl)imidazolinium chloride (DOTIM), or combinations thereof.

6. The composition according to claim 1, further comprising an emulsifier.

7. The composition according to claim 6, wherein said emulsifier comprises mannide oleate, mannide monooleate, lecithin, polysorbate 80, sorbitan laurate, sorbitan monooleate, sorbitan sesquioleate, sorbitan trioleate, or combinations thereof.

8. The composition according to claim 1, further comprising an adjuvant.

9. The composition according to claim 8, wherein said adjuvant is present: (a) within said liposomes; (b) exterior to said liposomes; or (c) both within said liposomes and exterior to said liposomes.

10. The composition according to claim 1, wherein said polynucleotide is inserted in an expression plasmid or is contained in a bacterial or viral vector.

11. The composition according to claim 1, wherein said polynucleotide is present both encapsulated within said liposomes and exterior to said liposomes.

12. The composition according to claim 1, wherein said polypeptide is an antigen, an antibody or antibody fragment, an enzyme, a cytokine, a therapeutic protein, a chemokine, a regulatory protein, a structural protein, a chimeric protein, a nuclear protein, a transcription factor, a viral protein, a TLR protein, an interferon regulatory factor, an angiostatic or angiogenic protein, an apoptotic protein, an Fc gamma receptor, a hematopoietic protein, a tumor suppressor, a cytokine receptor, or a chemokine receptor.

13. A method for delivering a polynucleotide to a subject, comprising administering the composition of claim 1 to said subject.

14. The method according to claim 13, wherein said subject is a human.

15. The composition according to claim 1, wherein said oil comprises a vegetable oil, mineral oil, a nut oil, soybean oil, or combinations thereof.

16. A method for making a composition comprising:
   (a) providing a polynucleotide that encodes a polypeptide and that is capable of being expressed in mammalian cells;
   (b) encapsulating said polynucleotide in liposomes comprising a saturated or unsaturated phospholipid; and
   (c) combining said liposomes with a carrier comprising a continuous phase of oil in a ratio of 1:1 by volume.

17. The method according to claim 16, wherein said liposomes are dehydrated before they are combined with said carrier.

18. The method according to claim 16, wherein said carrier is a water-in-oil emulsion.

19. The method according to claim 16, wherein said carrier is free of water.

20. The method according to claim 16, wherein said oil comprises a natural oil, a synthetic oil, or a combination thereof.

21. The method according to claim 16 wherein said liposomes comprise cholesterol, dioleoyl phosphatidylcholine (DOPC), phosphoglycerol, phosphoethanolamine, phosphoserine, phosphocholine, phosphoinositol, phosphatidylcholine, lecithin, phosphatidylcholine and ascorbyl palmitate, 1,2-dioleoyl-3-trimethylammonium-propane (DOTAP),1-[2-(oleoyloxy)ethyl]-2-oleyl-3-(2-hydroxyethyl)imidazolinium chloride (DOTIM), or combinations thereof.

22. The method according to claim 16, wherein said carrier comprises an emulsifier.

23. The method according to claim 22, wherein said emulsifier comprises mannide oleate, mannide monooleate, lecithin, polysorbate 80, sorbitan laurate, sorbitan monooleate, sorbitan sesquioleate, sorbitan trioleate, or combinations thereof.

24. The method according to claim 16, further comprising combining an adjuvant with said polynucleotides, said liposomes, or said carrier.

25. The method according to claim 16, wherein said polypeptide is an antigen, an antibody or antibody fragment, an enzyme, a cytokine, a therapeutic protein, a chemokine, a regulatory protein, a structural protein, a chimeric protein, a nuclear protein, a transcription factor, a viral protein, a TLR protein, an interferon regulatory factor, an angiostatic or angiogenic protein, an apoptotic protein, an Fc gamma receptor, a hematopoietic protein, a tumor suppressor, a cytokine receptor, or a chemokine receptor.

26. A composition produced by the method according to claim 16.

27. The method according to claim 16, wherein said oil comprises a vegetable oil, mineral oil, a nut oil, soybean oil, or combinations thereof.

* * * * *